United States Patent
Ohlmeyer et al.

(10) Patent No.: US 11,512,052 B2
(45) Date of Patent: Nov. 29, 2022

(54) DIHYDROPYRIDINES FOR THE TREATMENT OF COGNITIVE IMPAIRMENT OR TRAUMATIC BRAIN INJURY

(71) Applicants: Icahn School of Medicine at Mount Sinai, New York, NY (US); The United States Government as represented by the Department of Veterans Affairs, Washington, DC (US)

(72) Inventors: Michael Ohlmeyer, New York, NY (US); Dongming Cai, New York, NY (US)

(73) Assignees: Icahn School of Medicine at Mount Sinai, New York, NY (US); The United States Government as Represented by the Department of Veterans Affairs, Washington, DC (US)

( * ) Notice: Subject to any disclaimer, the term of this patent is extended or adjusted under 35 U.S.C. 154(b) by 114 days.

(21) Appl. No.: 16/763,962

(22) PCT Filed: Nov. 20, 2018

(86) PCT No.: PCT/US2018/062020
§ 371 (c)(1),
(2) Date: May 13, 2020

(87) PCT Pub. No.: WO2019/104041
PCT Pub. Date: May 31, 2019

(65) Prior Publication Data
US 2021/0230117 A1    Jul. 29, 2021

Related U.S. Application Data

(60) Provisional application No. 62/588,983, filed on Nov. 21, 2017.

(51) Int. Cl.
*C07D 211/90* (2006.01)
*A61P 25/28* (2006.01)

(52) U.S. Cl.
CPC ............ *C07D 211/90* (2013.01); *A61P 25/28* (2018.01)

(58) Field of Classification Search
CPC .................................................. C07D 211/90
See application file for complete search history.

(56) References Cited

U.S. PATENT DOCUMENTS 5,328,931 A    7/1994    Rosen et al.

FOREIGN PATENT DOCUMENTS

| EP | 0657430 | * 11/1994 | ........... C07D 211/90 |
| EP | 0657430 A1 | 6/1995 | |
| WO | PCT/US2018/062020 | 11/2018 | |
| WO | WO-2019/104041 A1 | 5/2019 | |

OTHER PUBLICATIONS

International Search Report and Written Opinion were dated Mar. 15, 2019 by the International Searching Authority for Application No. PCT/US2018/062020 dated Nov. 20, 2018 and published as WO 2019/104041 dated May 31, 2019 (10 pages).
PubChem CID 10835725, Created Oct. 26, 2006.
U.S. Appl. No. 62/588,983, filed Nov. 21, 2017, Michael Ohlmeyer, et al.

* cited by examiner

*Primary Examiner* — Paul V Ward
(74) *Attorney, Agent, or Firm* — Ballard Spahr LLP

(57) ABSTRACT

A genus of dihydropyridine chemical modulators of synaptojanin is disclosed. These modulators are selective inhibitors of synaptojanin 1 and may be used to treat cognitive impairment or traumatic brain injury, including promoting regeneration in cases of traumatic brain injury, or for treating neurodegenerative disorders.

20 Claims, 11 Drawing Sheets

DIHYDROPYRIDINES FOR THE TREATMENT OF COGNITIVE IMPAIRMENT OR TRAUMATIC BRAIN INJURY

CROSS-REFERENCE TO RELATED APPLICATIONS

This Application is a U.S. National Phase of International Application No. PCT/US2018/062020, filed Nov. 20, 2018, which claims the benefit of U.S. Provisional Application No. 62/588,983, filed Nov. 21, 2017, the contents of which are incorporated herein by reference in their entireties.

GOVERNMENT RIGHTS STATEMENT

This invention was made with U.S. Government support under 1I21RX001558 and 1I01RX002290 awarded by United States Department of Veteran's Affairs. The U.S. Government has certain rights in the invention.

BACKGROUND OF THE INVENTION

Technical Field

The invention relates to the use of dihydropyridine chemical modulators of synaptojanin 1 to treat cognitive impairment or traumatic brain injury. These modulators may be used for promoting regeneration in cases of traumatic brain injury, or for treating neurodegenerative disorders.

Background Information

Neurodegenerative disorders, such as Alzheimer's disease (AD), are a pervasive and growing problem. Neurodegenerative disorders relate to conditions that affect neurons, which can be damaged or destroyed in these disorders. Since neurons typically cannot regenerate, these conditions lead to often irreversible problems, resulting in problems with cognitive function, motor function, or both.

Alzheimer's disease (AD), the most prevalent neurodegenerative disease of aging, affects one in eight older Americans. Recent evidence indicates that sporadic AD (which accounts for 90% of AD) is likely caused by an impaired Aβ clearance. Mild cognitive impairment (MCI) is a condition in which slight decreases are seen in cognitive function, such as memory (i.e., amnestic MCI) or thinking or language skills (or non-amnestic MCI). The changes seen in MCI are noticeable, but do not generally interfere with daily activities of the afflicted person nor require assisted living; because of this, MCI is distinguished from dementia. Traumatic brain injury (TBI) is one of the most consistently identified environmental risks for late-onset neurodegeneration and sporadic AD. Individuals who suffer a TBI are two- to four-times more likely to develop AD.

Traumatic brain injury (TBI) can be triggered by a variety of causes. Common causes include falls, being struck by an object, motor vehicle crashes, blast wave exposure (e.g., in military veterans), and contact sport athletics. Traumatic brain injury is further characterized by its severity: mild traumatic brain injury (mTBI), such as a concussion, typically results in symptoms that last for a relatively short period of time, while severe traumatic brain injury generally results in an extended period of negative effects. Common symptoms of TBI include memory lapse or loss, loss of consciousness, headaches, impaired movement, compromised senses, dementia, and depression or other emotional changes.

Synaptojanin 1 (synj1) is the main phosphoinositol bisphosphate ($PIP_2$) degrading enzyme in the brain and synapses. Recent literature suggests that $PIP_2$ and synj1 are involved in the pathogenesis of AD, and that changes in synj1 protein levels correlate with human AD disease severity. Data suggests beneficial effects of synj1 reduction on AD brains, including accelerated amyloid clearance, ameliorated ApoE4 pathogenic effects, the rescue of AD-related lysosomal defects, and reduced mild traumatic brain injury (mTBI)-associated tau pathology, which could lead to cognitive improvement and could slow or reverse neurodegenerative processes in AD (and other neurodegenerative diseases) and in traumatic brain injury.

Certain calcium channel blockers possess characteristics that suggest an approach to treating neurodegenerative disorders. Nimodipine, a dihydropyridine calcium channel blocker originally developed for the treatment of high blood pressure, may act as a neuroprotector in neurodegenerative diseases that are inflammation-mediated. It has been shown that nimodipine promotes amyloid beta (Aβ) clearance and rescues Alzheimer's disease-related cognitive deficits through reduction of brain synj1 expression. Unfortunately, however, calcium channel blockers exhibit a number of side effects that would be disadvantageous in treating neurodegenerative diseases. Among the most common are dizziness, headache, nausea, peripheral edema, rash, and heart palpitations. In particular, clinical trials of nimodipine suggest that it may adversely impair cognitive function. This poses a concern for clinical development of dihydropyridines for treatment of neurodegenerative diseases and cognitive impairment. However, if calcium channel blockade can be separated from synaptojanin 1 inhibition, the dihydropyridine scaffold could provide a starting point for the development of small molecule therapies for treatment of neurodegenerative diseases. Dihydropyridine calcium channel blockers other than nimodipine, for example nifedipine, do not show the same beneficial effects on AD brains, which suggests that synaptojanin 1-lowering effects may be separated from calcium channel blocker activity. Compounds that separated synaptojanin 1-lowering effects from calcium channel blocker activity in such a way that synaptojanin 1-lowering was maximized and calcium channel blocking was minimized would be highly beneficial.

SUMMARY OF THE INVENTION

The present invention provides, in a first aspect, a compound of formula I:

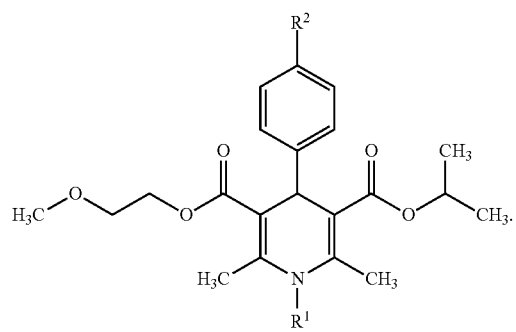

wherein

R[1] is selected from hydrogen, $C_1$-$C_6$ alkyl, and $C_3$-$C_6$ cycloalkyl; and R[2] is selected from hydrogen, halogen, $C_1$-$C_6$ alkyl, $C_3$-$C_6$ cycloalkyl, $C_1$-$C_6$ alkoxy, $C_1$-$C_6$ haloalkoxy, $C_1$-$C_6$ haloalkyl, nitro, cyano, $C_1$-$C_6$ alkylthio, and $C_1$-$C_6$ haloalkylthio.

The present invention provides, in a second aspect, methods and uses of the above-described compounds in medicine, particularly for the treatment of cognitive impairment or traumatic brain injury in a patient. These methods include administering to a patient a therapeutically effective amount of a compound described herein.

The present invention provides, in a third aspect, a method of inhibiting synaptojanin 1 expression. The method includes contacting synaptojanin 1 with an effective amount of compound of formula I at a concentration effective to inhibit synaptojanin 1 activity.

The present invention provides, in a fourth aspect, a method of inhibiting synaptojanin 1 activity. The method includes contacting synaptojanin 1 with an effective amount of compound of formula I at a concentration effective to inhibit synaptojanin 1 activity.

The present invention provides, in a fifth aspect, a method of selectively inhibiting synaptojanin 1. The method includes contacting synaptojanin 1 with an amount of a compound of formula I less than the amount required to inhibit calcium channels.

The present invention provides, in a sixth aspect, methods and uses of the above-described compounds in medicine, particularly for treating a disease or disorder in a patient by down-regulating synaptojanin 1. These methods and uses include administering to a patient a therapeutically effective amount of a compound described herein.

The present invention provides, in a seventh aspect, pharmaceutical compositions comprising the compounds described herein.

These, and other objects, features and advantages of this invention will become apparent from the following detailed description of the various aspects of the invention taken in conjunction with the accompanying drawings.

DETAILED DESCRIPTION OF THE INVENTION

Figure 1:
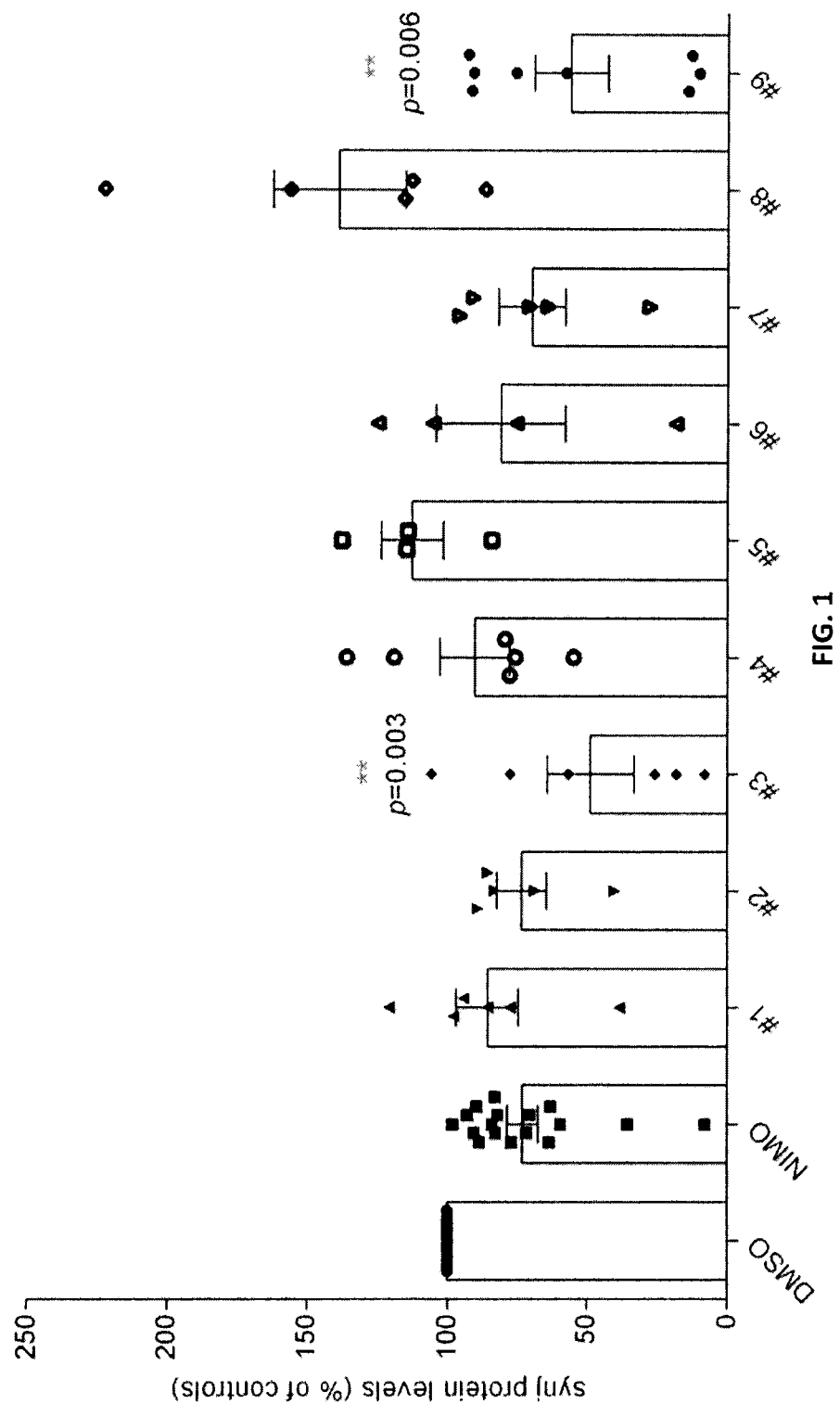
FIG. 1 shows the effect on synj1 protein levels as a percentage of the control after administration of compounds of the invention in wt (wild type) cortical neurons.

A need exists for novel compounds related to nimodipine that will be beneficial for treating cognitive impairment or traumatic brain injury, such as mTBI and AD and other neurodegenerative diseases and disorders. Herein are disclosed a series of novel dihydropyridine (DHP) compounds related to nimodipine. These compounds have attenuated calcium channel blocker activity, to minimize side effects, while retaining the synaptojanin 1-lowering effects of nimodipine and, in some instances, increasing the potency against synj1 and Aβ compared to nimodipine both in vitro and in vivo.

In some embodiments, the invention relates to compounds of formula I:

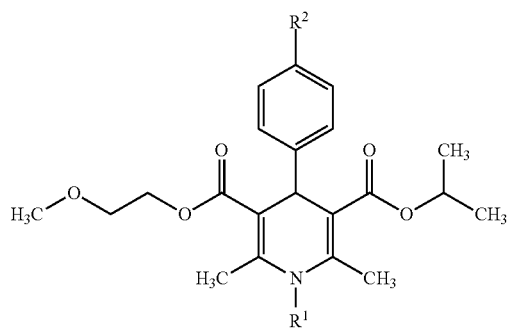

as described above.

In some embodiments, the invention relates to compounds of formula IA:

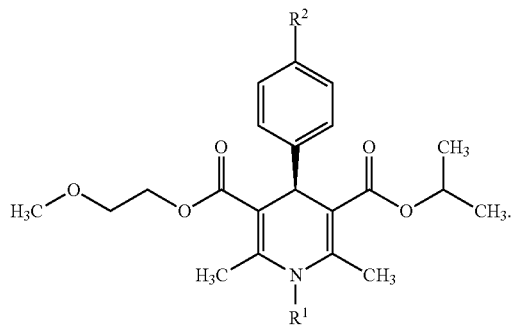

In some embodiments, the invention relates to compounds of formula IB:

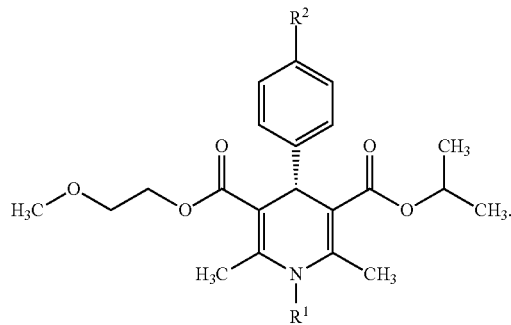

In the embodiments described below, the compound may be of formula I, formula IA, or formula IB, unless otherwise indicated.

In some embodiments, $R^1$ is hydrogen. In other embodiments, $R^1$ is $C_1$-$C_6$ alkyl. In some embodiments, $R^1$ is methyl, ethyl, n-propyl, or isopropyl. In still other embodiments, $R^1$ is $C_3$-$C_6$ cycloalkyl. In some embodiments, $R^1$ is cyclopropyl.

In some embodiments, $R^2$ is hydrogen. In other embodiments, $R^2$ is halogen. In still other embodiments, $R^2$ is fluoro, and in some embodiments, $R^2$ is chloro. In some embodiments, $R^2$ is $C_1$-$C_6$ alkyl. In other embodiments, $R^2$ is t-butyl, or n-propyl, or isopropyl, or ethyl, or methyl. In still other embodiments, $R^2$ is t-butyl. In some embodiments, $R^2$ is $C_3$-$C_6$ cycloalkyl. In some embodiments, $R^2$ is cyclopropyl, cyclobutyl, cyclopentyl or cyclohexyl. In some embodiments, $R^2$ is $C_1$-$C_6$ alkoxy. In other embodiments, $R^2$ is methoxy. In yet other embodiments, $R^2$ is $C_1$-$C_6$ haloalkoxy. In other embodiments, $R^2$ is $C_1$-$C_3$ perfluoroalkoxy. In still other embodiments, $R^2$ is trifluoromethoxy. In some embodiments, $R^2$ is $C_1$-$C_6$ haloalkyl. In other embodiments, $R^2$ is $C_1$-$C_3$ perfluoroalkyl. In still other embodiments, $R^2$ is trifluoromethyl. In other embodiments, $R^2$ is $C_1$-$C_6$ alkylthio. In still other embodiments, $R^2$ is —$SCH_3$. In some embodiments, $R^2$ is $C_1$-$C_6$ haloalkylthio. In other embodiments, $R^2$ is —$SCF_3$. In some embodiments, $R^2$ is nitro. In still other embodiments, $R^2$ is cyano, In some embodiments, $R^1$ is hydrogen and $R^2$ is selected from hydrogen, fluoro, chloro, methoxy, trifluoromethyl, trifluoromethoxy, and t-butyl. In other embodiments, $R^1$ is methyl and $R^2$ is selected from hydrogen, fluoro, chloro, methoxy, trifluoromethyl, trifluoromethoxy, and t-butyl.

In some embodiments of the foregoing subgenera, compounds can be either single enantiomers, like in formulae IA and IB, or a mixture of the two. If a mixture, the mixture will most commonly be racemic, but it need not be. Substantially pure single enantiomers of biologically active compounds such as those described herein often exhibit advantages over their racemic mixture.

The compounds described herein contain at least one asymmetric center and may thus give rise to enantiomers, diastereomers, and other stereoisomeric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, the representations:

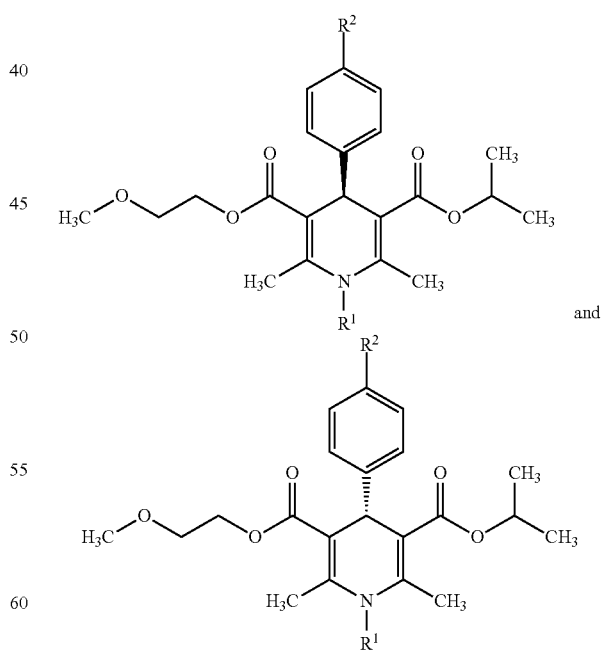

indicate each single enantiomer of known absolute stereochemistry, i.e., each of the two structures is a substantially pure single enantiomer. For the purpose of the present disclosure, a "pure" or "substantially pure" enantiomer is intended to mean that the enantiomer is at least 95% of the configuration shown and 5% or less of other enantiomers. The graphic representation:

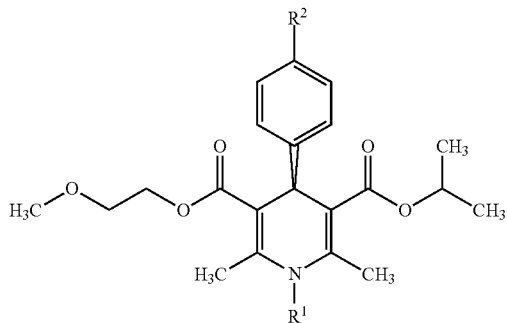

indicates a single enantiomer of unknown absolute stereochemistry, i.e., it could be either of the two structures shown above, as a substantially pure single enantiomer. And, finally, the structure:

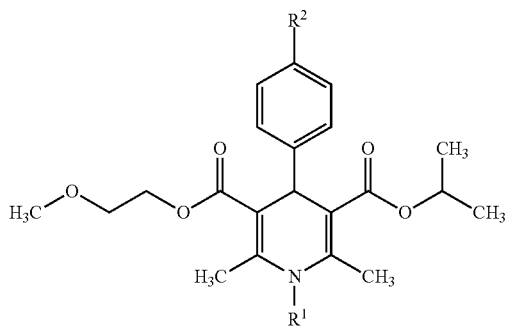

conveys no information regarding stereochemistry. This structure could be a single enantiomer or a mixture of enantiomers, including a racemic mixture.

It may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genus I that are not in the public's possession.

Also provided herein is a pharmaceutical composition comprising a compound disclosed above, or a pharmaceutically acceptable salt form thereof, and a pharmaceutically acceptable carrier or diluent.

While it may be possible for the compounds of the formulae disclosed herein to be administered as the raw chemical, it is preferable to present them as a pharmaceutical composition. According to a further aspect, the present invention provides a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

Formulations of the compounds and compositions described herein may be administered by a variety of methods: oral (including, but not limited to, capsules, cachets, tablets, powder, granules, solutions, suspensions, emulsions, tablets, or sublingual tablets), buccal, by inhalation (by using, for instance, an inhaler, a nebulizer, an aerosol, a gas, etc.), nasal, topical (including, but not limited to, lotions, creams, ointments, patches (i.e., transdermal), gels, liniments, pastes), ophthalmic, to the ear, rectal (for instance, by using a suppository or an enema), vaginal, or parenteral (i.e., injectable), depending on the severity and type of the disease being treated.

In some embodiments, the compositions are administered orally, transdermally, or intravenously. The formulations include those suitable for oral, parenteral (including subcutaneous, intradermal, intramuscular, intracranial, intravenous and intraarticular), rectal, vaginal, nasal (inhalation), and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations of the present invention may be suitable for topical or transdermal administration. These dosage forms for administration of a compound of this invention include patches, ointments, creams, lotions, gels, pastes, solutions, sprays, inhalants, or powders. Formulations of the present invention may be administered by transdermal patches, allowing for controlled delivery of an active ingredient to a subject. The compound of the invention is mixed (i.e., dissolved or dispensed) with a pharmaceutically acceptable carrier. Buffers, absorption enhancers, and/or preservatives may also be desired for inclusion. Rate controlling membranes or polymer matrices or gels may be used to control the absorption rate. Ophthalmic formulations, ear drops, and eye drops are also contemplated as being within the scope of this invention.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Abbreviations and Definitions

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

The following abbreviations and terms have the indicated meanings throughout:
Ac=acetyl
Aq=aqueous
Boc=t-butyloxy carbonyl
Bu=butyl
c-=cyclo
cat=catalyst
Cbz=carboxybenzyl
DBA=dibenzylideneacetone
DCM=dichloromethane=methylene chloride=$CH_2Cl_2$
DMF=N,N-dimethylformamide
DMSO=dimethyl sulfoxide
eq. or equiv.=equivalent(s)
Et=ethyl
GC=gas chromatography
h=hour(s)
KHMDS=Potassium bis(trimethylsilyl)amide
LG=leaving group
Ln=chiral ligands
mCPBA=meta-Chloroperoxybenzoic acid
Me=methyl
mesyl=methanesulfonyl
min.=minute(s)
Mol. Wt.=molecular weight
Ms=mesylate
NMO or NMMO=N-methylmorpholine oxide
Pg=protecting group
Ph=phenyl
RT=room temperature
sat'd or sat.=saturated
t- or tert=tertiary
Tf=triflate
TFA=trifluoroacetic acid
Tg=transgenic
THF=tetrahydrofuran
tosyl=p-toluenesulfonyl
wt=wild type Throughout this specification the terms and substituents retain their definitions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or composition that "comprises", "has", "includes" or "contains" one or more steps or elements possesses those one or more steps or elements, but is not limited to possessing only those one or more steps or elements. Likewise, a step of a method or an element of a composition that "comprises", "has", "includes" or "contains" one or more features possesses those one or more features, but is not limited to possessing only those one or more features. The terms "comprising" and "including" or grammatical variants thereof are to be taken as specifying the stated features, integers, steps or components but do not preclude the addition of one or more additional features, integers, steps, components or groups thereof. For example, "X includes a, b and c" means that X includes, but is not limited to, a, b and c. This term encompasses the terms "consisting of" and "consisting essentially of".

Unless otherwise specified, the phrase "such as" is intended to be open-ended. For example, "X can be a halogen, such as fluorine or chlorine" means that X can be, but is not limited to, fluorine or chlorine.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. For the purpose of this application, alkoxy includes methylenedioxy and ethylenedioxy.

The term "halogen" means fluorine, chlorine, bromine or iodine atoms. In one embodiment, halogen may be a fluorine or chlorine atom.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(O)alkoxy, respectively.

As used herein, and as would be understood by the person of skill in the art, the recitation of "a compound"—unless expressly further limited—is intended to include salts of that compound. In a particular embodiment, the term "compound" (as in, for instance, "compound of formula") refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

The terms "subject" or "subject in need thereof" or "patient" are used interchangeably herein. These terms refer to a patient who has been diagnosed with the underlying disorder to be treated. The subject may currently be experiencing symptoms associated with the disorder or may have experienced symptoms in the past. Additionally, a "subject in need thereof" may be a patient at risk of developing a particular disease, or to a patient reporting one or more of the physiological systems of a disease, even though a diagnosis of this disease may not have been made. As a non-limiting example, a "subject in need thereof", for purposes of this application, may include a patient who is currently diagnosed with Alzheimer's disease or was diagnosed with Alzheimer's disease in the past, regardless of current symptomatology. A "subject in need thereof" can also include a patient who is showing cognitive deficits, but has not been diagnosed with a particular disorder.

A "patient," as used herein, includes both humans and other animals, particularly mammals. Thus, the methods are applicable to both human therapy and veterinary applications. In some embodiments, the patient is a mammal, for example, a primate. In some embodiments, the patient is a human.

As used herein, the terms "treatment" or "treating" are used interchangeably. These terms refer to an approach for obtaining beneficial or desired results including, but not limited to, therapeutic benefit. Therapeutic benefit includes eradication or amelioration of the underlying disorder being treated; it also includes the eradication or amelioration of one or more of the symptoms associated with the underlying disorder such that an improvement is observed in the patient, notwithstanding that the patient may still be afflicted with the underlying disorder.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The compounds of the invention can be used to treat cognitive impairment (also referred to herein as "neurodegenerative disorder" or "neurodegenerative disease"), such as that found in Alzheimer's disease, other dementias (such as vascular dementia, frontotemporal dementia (FTD), Lewy body dementia (LDB), or mixed dementia), mild cognitive impairment (MCI), and Down Syndrome. The compounds of the invention can be used to treat traumatic brain injury (TBI). There is a relationship between TBI, Alzheimer's disease (AD), and dementia. People who suffer a TBI are two- to four-times more likely to develop late-onset neurodegeneration and AD.

Alzheimer's disease (AD) is characterized neuropathologically by senile plaques containing β-amyloid peptides (Aβ), as well as neurofibrillary tangles consisting of hyperphosphorylated tau. Either overproduction or impaired clearance of Aβ can lead to Aβ accumulation. Recent evidence suggests that late-onset AD cases (accounting for 90% of AD cases) are correlated with an overall impairment in Aβ clearance. Furthermore, several studies report pathological changes of the endosomal/lysosomal network, which develop in neurons as Alzheimer's disease progresses, and include dysregulation of endocytosis and progressive failure of lysosomal clearance mechanisms. A close connection between lysosomal protein clearance failure and mechanisms of neurodegeneration is also well documented.

Endosomal anomalies are considered one of the earliest AD pathologies, and increased function of synj1 is linked to enlargement of early endosomes. Most importantly, it has been found that down-regulation of synj1 increases Aβ uptake and lysosomal trafficking, thereby stimulating Aβ clearance. Furthermore, reduction of synj1 attenuates amyloid-induced neuropathologic changes and behavior deficits in an AD transgenic mouse model.

The Alzheimer's Association estimates that MCI afflicts 15-20% of people 65 years of age or older. It is thought that the risk factors that lead to MCI are similar to those for dementia and Alzheimer's disease (AD); these include advancing age, cardiovascular disease (or risk factors leading to it), and/or familial history of dementia or AD. Additionally, individuals who have MCI are at an increased risk for developing AD or dementia than non-MCI-afflicted individuals. People who are carriers of the ApoE4 gene are also thought to be at a higher risk of developing MCI and/or AD. The compounds of the invention can be used to treat patients who carry the ApoE4 gene, patients with MCI, and/or patients with pre-clinical or active AD.

Down syndrome (DS) occurs once in approximately every 700 births in the United States and is caused by an extra copy of at least a portion of chromosome 21.

Synaptojanin 1 has been implicated as being involved in Down syndrome, perhaps because its gene, SYNJ1, is believed to be located on human chromosome 21. Individuals affected with DS commonly develop Alzheimer's disease.

TBI may also be treated by compounds of the invention. According to the Centers for Disease Control, traumatic brain injury (TBI) sufferers were seen in U.S. emergency rooms 2.5 million times in 2010. Neuropathological studies of human TBI cases have described the development of neurofibrillary tangles and amyloid plaques associated with neurodegenerative processes.

Without being held to any one theory, data suggest that ApoE proteins regulate changes in brain phospholipid homeostasis in response to blast TBI and that the ApoE4 isoform is dysfunctional in this process. Down-regulation of synj1 has been shown to rescue blast-induced phospholipid dysregulation and prevent development of Tau hyper-phosphorylation in ApoE4 carriers.

Substituents are generally defined when introduced and retain that definition throughout the specification and in all independent claims.

Compounds of the invention that have been made are shown below in TABLE I:

TABLE I

| Example No. | Structure |
|---|---|
| 1 | 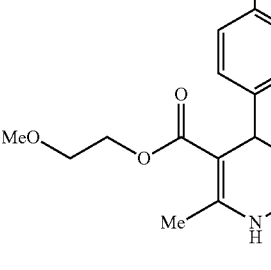 |
| 2 | 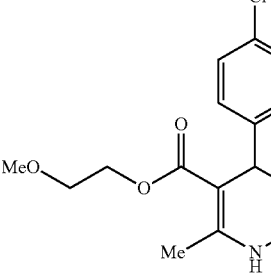 |
| 3 | 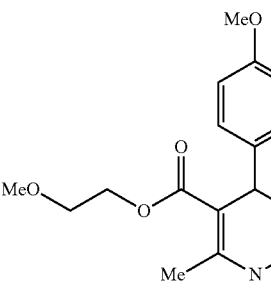 |
| 4 | 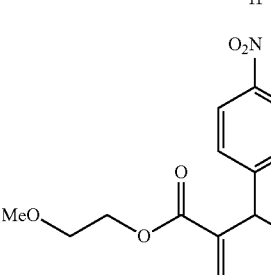 |
| 5 | 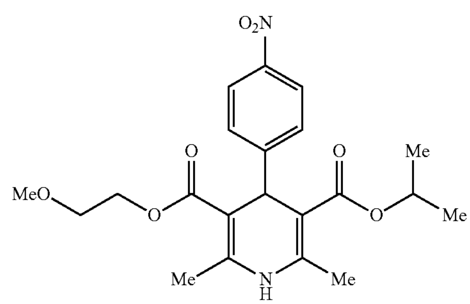 [SMILES: COCCOC(=O)C1=C(C)NC(C)=C(C(=O)OC(C)C)C1c1ccc([N+](=O)[O-])cc1] |
| 6 | 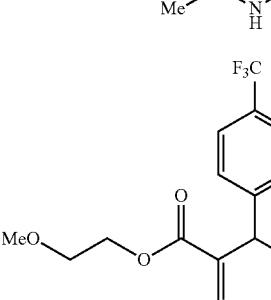 |

TABLE I-continued

| Example No. | Structure |
|---|---|
| 7 | 4-(4-trifluoromethoxyphenyl)-3-(2-methoxyethyl) 5-isopropyl 2,6-dimethyl-1,4-dihydropyridine-3,5-dicarboxylate |
| 8 | 4-(4-methylphenyl)-3-(2-methoxyethyl) 5-isopropyl 2,6-dimethyl-1,4-dihydropyridine-3,5-dicarboxylate |
| 9 | 4-(4-tert-butylphenyl)-3-(2-methoxyethyl) 5-isopropyl 2,6-dimethyl-1,4-dihydropyridine-3,5-dicarboxylate |

Compounds that could be made by methods disclosed herein are shown in TABLE II:

TABLE II

| Compound ID | Structure |
|---|---|
| 20 | 4-(4-nitrophenyl)-3-(2-methoxyethyl) 5-isopropyl 1,2,6-trimethyl-1,4-dihydropyridine-3,5-dicarboxylate |
| 21 | 4-phenyl-3-(2-methoxyethyl) 5-isopropyl 1,2,6-trimethyl-1,4-dihydropyridine-3,5-dicarboxylate |
| 22 | 4-(4-trifluoromethylphenyl)-3-(2-methoxyethyl) 5-isopropyl 1,2,6-trimethyl-1,4-dihydropyridine-3,5-dicarboxylate |
| 23 | 4-(4-methoxyphenyl)-3-(2-methoxyethyl) 5-isopropyl 1,2,6-trimethyl-1,4-dihydropyridine-3,5-dicarboxylate |
| 24 | 4-(4-methylphenyl)-3-(2-methoxyethyl) 5-isopropyl 1,2,6-trimethyl-1,4-dihydropyridine-3,5-dicarboxylate |

TABLE II-continued
| Compound ID | Structure |
|---|---|
| 25 | 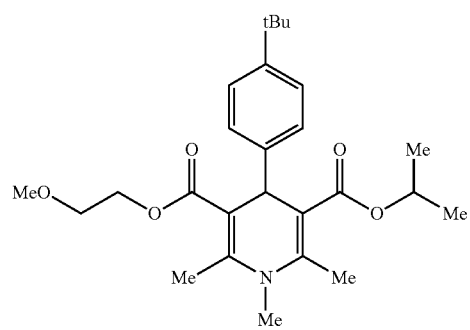 [SMILES: COCCOC(=O)C1=C(C)N(C)C(C)=C(C(=O)OC(C)C)C1c1ccc(C(C)(C)C)cc1] |
| 26 | 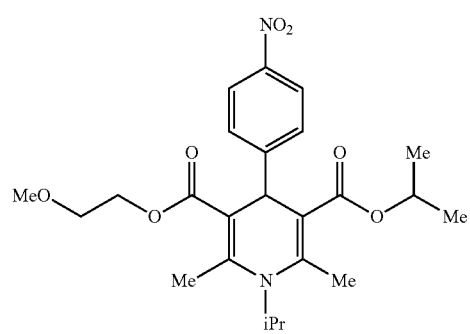 [SMILES: COCCOC(=O)C1=C(C)N(C(C)C)C(C)=C(C(=O)OC(C)C)C1c1ccc([N+](=O)[O-])cc1] |
| 27 | 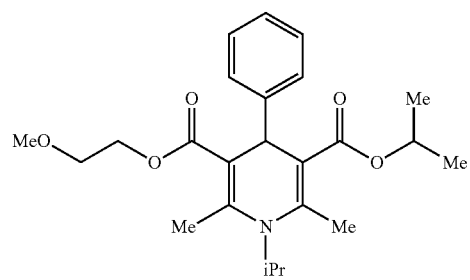 [SMILES: COCCOC(=O)C1=C(C)N(C(C)C)C(C)=C(C(=O)OC(C)C)C1c1ccccc1] |
| 28 | 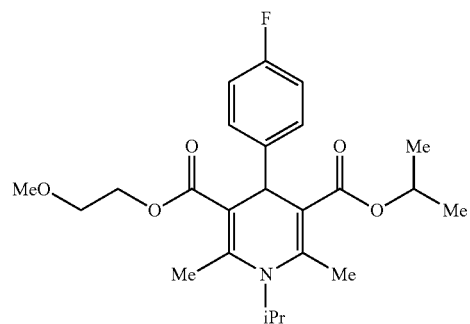 |
| 29 | 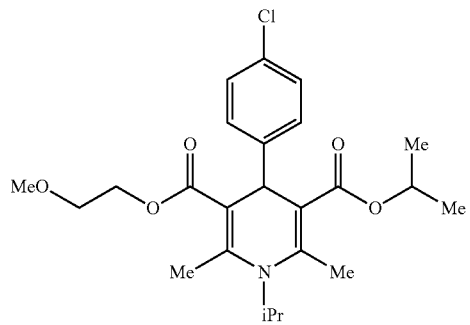 [SMILES: COCCOC(=O)C1=C(C)N(C(C)C)C(C)=C(C(=O)OC(C)C)C1c1ccc(F)cc1] |
| 30 | 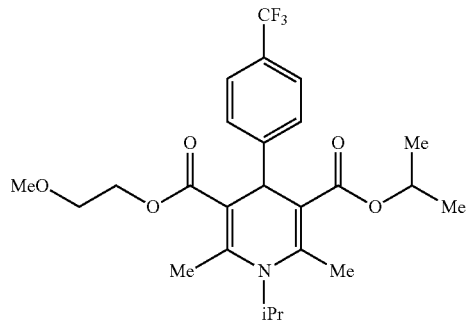 [SMILES: COCCOC(=O)C1=C(C)N(C(C)C)C(C)=C(C(=O)OC(C)C)C1c1ccc(C(F)(F)F)cc1] |
| 31 | 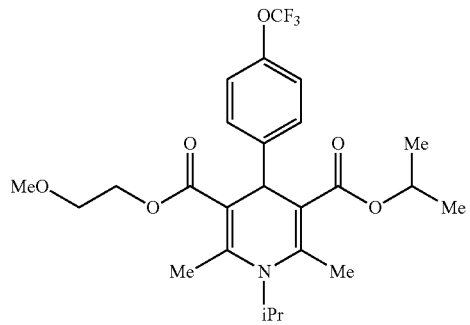 [SMILES: COCCOC(=O)C1=C(C)N(C(C)C)C(C)=C(C(=O)OC(C)C)C1c1ccc(OC(F)(F)F)cc1] |
| 32 | 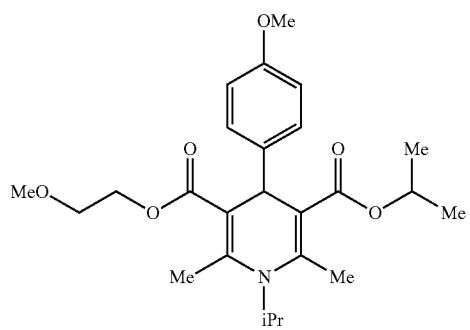 [SMILES: COCCOC(=O)C1=C(C)N(C(C)C)C(C)=C(C(=O)OC(C)C)C1c1ccc(OC)cc1] |

TABLE II-continued

| Compound ID | Structure |
|---|---|
| 33 | 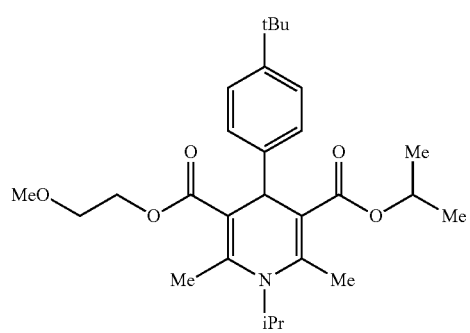 |
| 34 | 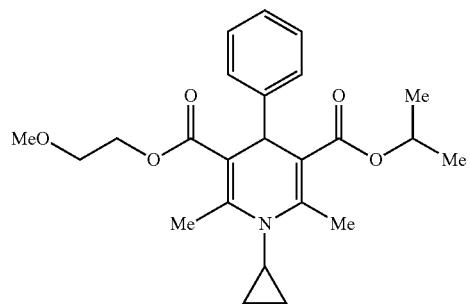 [SMILES: COCCOC(=O)C1=C(C)N(C2CC2)C(C)=C(C(=O)OC(C)C)C1c1ccccc1] |
| 35 | 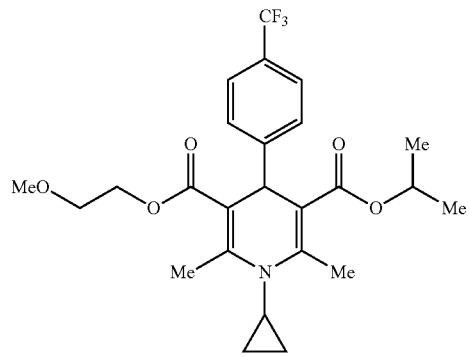 |
| 36 | 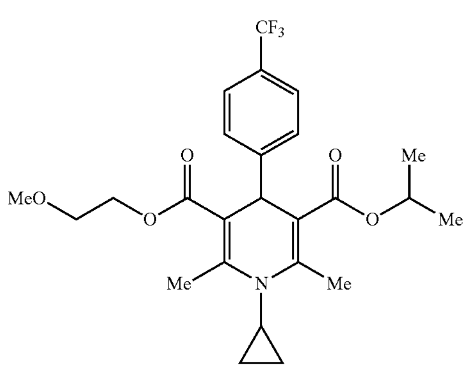 [SMILES: COCCOC(=O)C1=C(C)N(C2CC2)C(C)=C(C(=O)OC(C)C)C1c1ccc(C(F)(F)F)cc1] |

TABLE II-continued

| Compound ID | Structure |
|---|---|
| 37 | 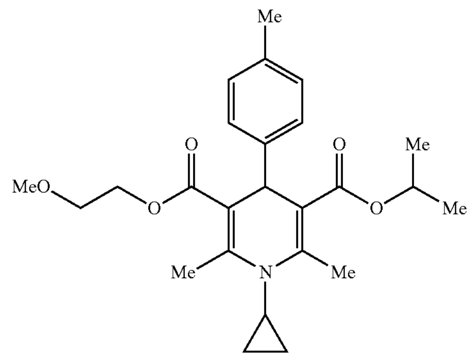 [SMILES: COCCOC(=O)C1=C(C)N(C2CC2)C(C)=C(C(=O)OC(C)C)C1c1ccc(C)cc1] |

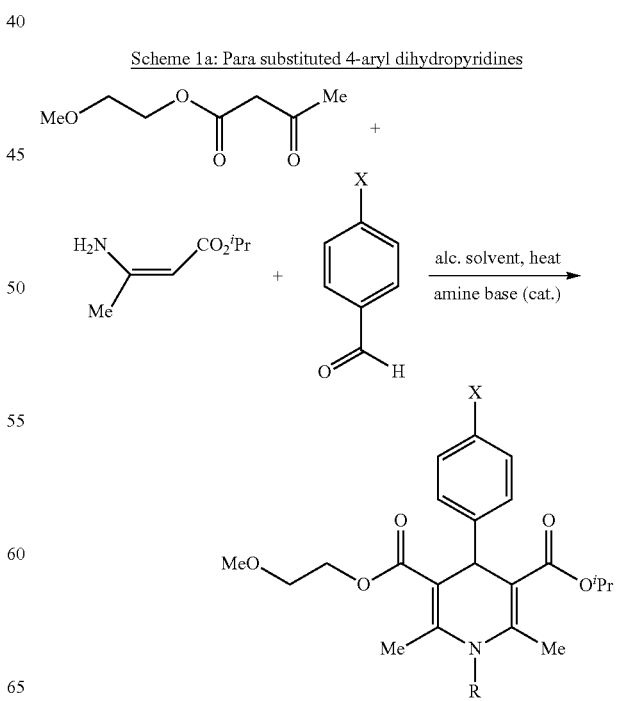

Synthesis

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, $1^{st}$ Ed., Oxford University Press, 2000; and in *March's Advanced Organic chemistry: Reactions, Mechanisms, and Structure*, $5^{th}$ Ed., Wiley-Interscience Publication, 2001.

Synthesis of the requisite compounds is well established and most readily accomplished by modifications of the Hantzsch synthesis described in, for example, Bossert et al. Approaches to the synthesis of the compounds of the present invention are shown in Scheme 1a and b:

Scheme 1a: Para substituted 4-aryl dihydropyridines

Scheme 1b: N-blocked dihydropyridines

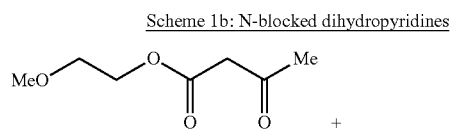

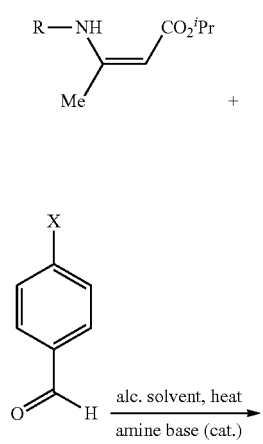

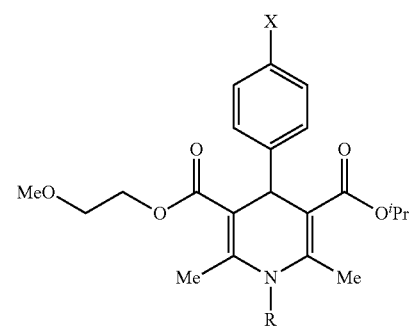

For example, 2-methoxyethyl 3-oxobutanoate is condensed with isopropyl (Z)-3-aminobut-2-enoate and a 4-substituted benzaldehyde in an alcoholic solvent such as methanol, ethanol or isopropanol with a catalytic amount of an amine base such as piperidine or morpholine for 1 to 24 hr at a temperature between ambient and reflux for the solvent in question. Concentration and silica gel chromatography or preparative HPLC affords para substituted 4-aryl dihydropyridines, as shown in Scheme 1a. Use of a 3-alkyl aminobut-2-enoate affords 1-substituted, i.e., N-blocked, dihydropyridines as shown in Scheme 1b.

Where the dihydropyridine nucleus is unsymmetrically substituted, as in the compounds of the present invention, the 4-position is a chiral center. Compounds may be prepared in racemic form or resolved into their enantiomers. In addition, several synthetic methods are known for the asymmetric synthesis of chiral dihydropyridine compounds, and these may be used for the synthesis of the compounds in either enantiomeric form, as in, for example, compounds of formula IA or formula IB. The chirality of the molecules will be of significance in so far as the molecular target for the synj1-lowering effects may recognize one enantiomer preferentially and this hand may not be the same as that preferred by the calcium channels or other off-target effects.

Exemplary syntheses are presented below.

EXAMPLES

Synthesis of 3-isopropyl 5-(2-methoxyethyl) 4-(4-(tert-butyl)phenyl)-2,6-dimethyl-1,4-dihydropyridine-3,5-dicarboxylate (Example 9)

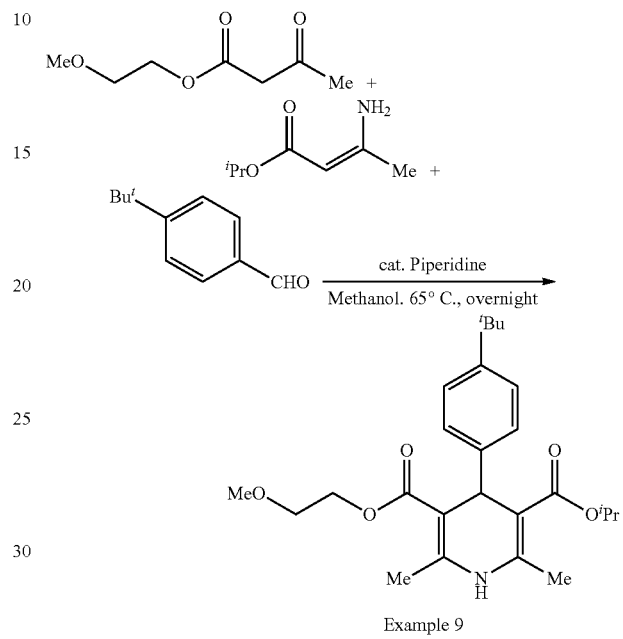

Example 9

A mixture of 2-methoxyethyl 3-oxobutanoate (1.0 g, 6.3 mmol), (Z)-isopropyl 3-aminobut-2-enoate (0.89 g, 6.3 mmol), 4-tert-butylbenzaldehyde (1.2 g, 6.3 mmol) and piperidine (1 drop) in methanol (10 Ml) was heated at 65° C. overnight. The solvent was removed and the residue was purified by silica gel column chromatography to give product, 3-isopropyl 5-(2-methoxyethyl) 4-(4-(tert-butyl)phenyl)-2,6-dimethyl-1,4-dihydropyridine-3,5-dicarboxylate (Example 9), 240 mg, 10% yield as a pale yellow oil. HPLC and LCMS (ES+) indicate >95% purity and MS consistent with product; MH$^+$ at 430.70 amu. $^1$H NMR (300 MHz, CDCl$_3$) δ 7.22 (4H, br s), 5.60 (1H, br s), 4.99-4.94 (2H, overlapping m), 4.26-4.15 (2H, m), 3.56 (2H, m), 3.36 (3H, s), 2.34 (6H, br s), 1.28 (9H, s), 1.25 (3H, d), 1.13 (3H, d).

Synthesis of 3-isopropyl 5-(2-methoxyethyl) 2,6-dimethyl-4-(4-(trifluoromethyl(phenyl)-1,4-dihydropyridine-3,5-dicarboxylate (Example 6)

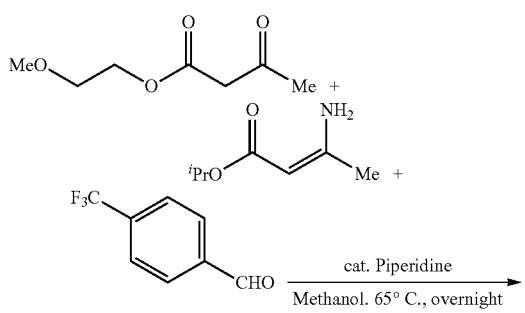

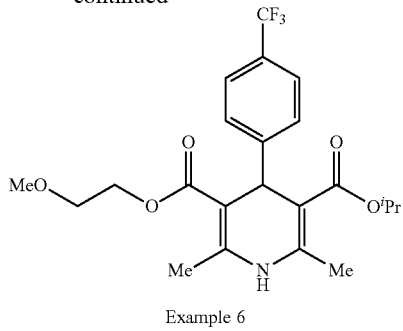

Example 6

The synthetic procedure is exactly analogous to that for Example 9. HPLC and LCMS (ES+) indicate >95% purity and MS consistent with product; MR+ at 440.41 amu. $^1$H NMR (300 MHz, CDCl$_3$) δ 7.42 (4H, br m), 5.69 (1H, br s), 5.05 (1H s), 4.93 (1H, m), 4.19 (2H, m), 3.54 (2H, m), 3.34 (3H, s), 2.34 (6H, br s) 1.26 (3H, d), 1.10 (3H, d).

Results
Summary Biological Profile of Example 9 Versus Nimodipine

| Parameter | Biological Activity of Example 9 vs Nimodipine |
| --- | --- |
| Activity in primary assay (luciferase assay) | Nimodipine at 10 μM achieved a 43.0% inhibition of synj1 transcription activities and Example 9 at 3 μM exhibited a 44.4% inhibition. |
| Activity in cell-based secondary assays (ELISA, western blot) | WT: Nimodipine at 10 μM achieved a 25.6% reduction of synj1 protein levels, a 47% reduction of Aβ40 levels and a 12.1% reduction of Aβ42 levels. Example 9 at 5 μM exhibited a 62.3% reduction of synj1 protein levels, an 82.6% reduction of Aβ40 levels, and a 46.4% reduction of Aβ42 levels. |
| Calcium Channel Activity Ca$^{2+}$- L type, Cerep (dihydropyridine site, antagonist, radioligand displacement) | Example 9 has attenuated calcium channel inhibition versus Nimodipine. Example 9 shows a 41.3% inhibition calcium channel inhibitory activities at 1 μM versus nimodipine which shows 99.6% inhibition. Example 9 shows no calcium channel inhibition at 1 nM versus Nimodipine which shows 93.4% inhibition at 1 nM |
| in vivo assays (behavior studies, ELISA and western blot) | Nimodipine at 2.5 mg/kg/day IP injection for 6 month achieved a 75.8% reduction of synj1 protein levels, a 11% decrease in insoluble Aβ$_{42}$ levels, a 16.8% decrease in soluble Aβ$_{42}$ levels, a 14.2% decrease in insoluble Aβ$_{40}$ levels and a 24.7% decrease in soluble Aβ$_{40}$ levels in APP/PS1 transgenic mouse brain neocortical regions compared to Tg vehicle controls. There was also functional rescue measured by NOR and Y-maze tests in nimodipine-treated AD mice. Example 9 achieved a 99.4% reduction of synj1 protein levels, a 27.4% decrease in insoluble Aβ$_{42}$ levels, a 19.3% decrease in soluble Aβ$_{42}$ levels, a 23.7% decrease in insoluble Aβ$_{40}$ levels and a 12% decrease in soluble Aβ$_{40}$ levels in APP/PS1 transgenic mouse brain neocortical regions compared to Tg vehicle controls. There was also functional rescue measured by NOR and Y-maze tests in nimodipine-treated AD mice. |

The effects of nimodipine derivatives on synj1 expression levels. Embryonic day 17 old wt cortical neurons were incubated with various compounds (example 1-9) for 72-96 hours before being subjected for Western blot analysis of synj1 protein levels. DMSO was used as a negative control, and nimodipine (NIMO) at 10 uM was used as a positive control. Example #1, 2, 3, 4, 5, and 8 were tested at 10 μM concentration, and example #6, 7 and 9 were tested at 5 μM concentration due to observed toxicities at 10 μM. Results were determined by measuring the synj1 protein levels as a percentage of the control (±SEM). One-way ANOVA was performed followed by post-hoc multiple comparison tests to determine the significance of differences between drug-treated vs DMSO control. **p<0.01; N=4-17/condition. (FIG. 1.)

Figure 2:
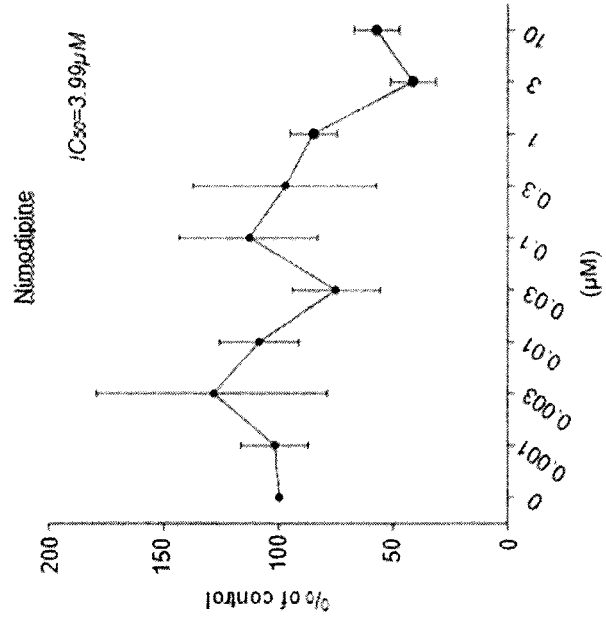
FIG. 2 depicts luciferase assays using synj1 5'-promoter regions tagged with luciferase transfected into ApoE4 neurons which were treated with nimodipine and compounds of the invention.
Figure 2:
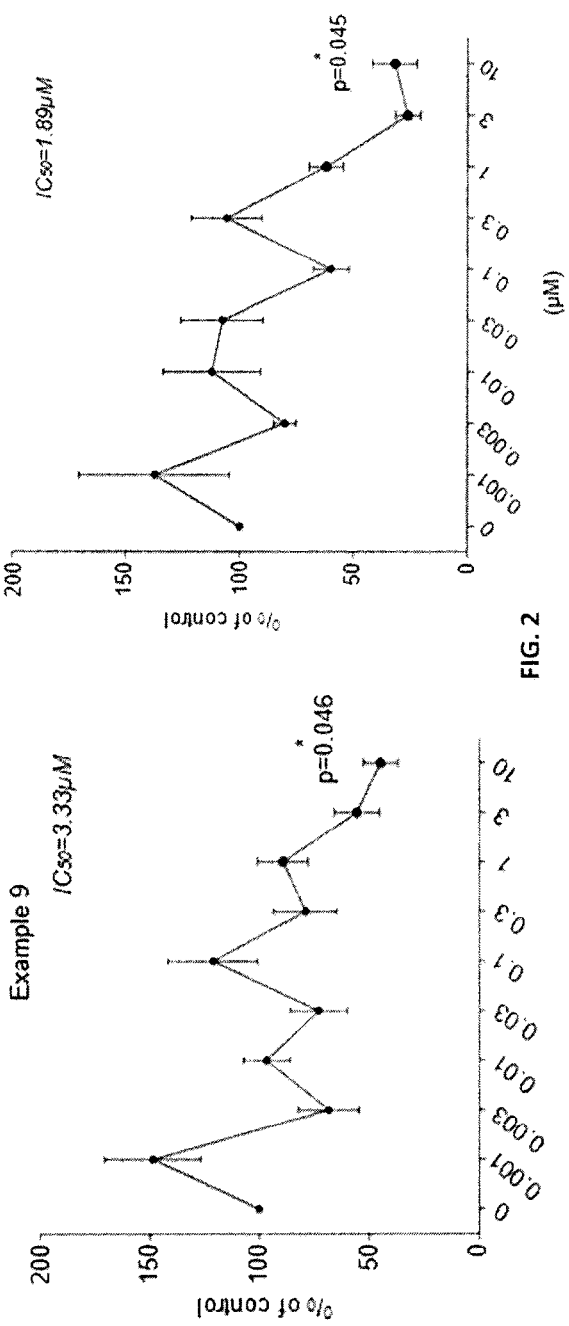

The effects of two nimodipine derivatives on synj1 transcriptional activities measured by luciferase assays. The in vitro luciferase assay uses a dual reporter system of Gaussia luciferase (GLuc) and secreted alkaline phosphatase (SEAP) tagged synj1 5'-promoter region. Embryonic day 17 old ApoE4 cortical neurons were transfected with a construct containing the synj1 5'-promoter region tagged with luciferase for 24 hours followed by treatment with various compounds (DMSO, nimodipine, Example 9 or Example 6) at various concentrations for another 48 hours before subjected for luciferase assays. (FIG. 2). DMSO-treated conditions were used as controls and results were presented as percentage of the control (±SEM). One-way ANOVA was performed followed by post-hoc multiple comparison tests to determine the significance of differences between drug-treated vs DMSO control. *p<0.05; N=5-17/condition. The IC$_{50}$ of the three compounds are: A) Nimodipine at 3.99 μM, B) Example 9 at 3.33 μM, and C) Example 6 at 1.89 μM. Example 9 and Example 6 both performed well, with Example 6 showing modestly increased potency at lowering synj1 in vitro as measured by luciferase assays.

Figure 3:
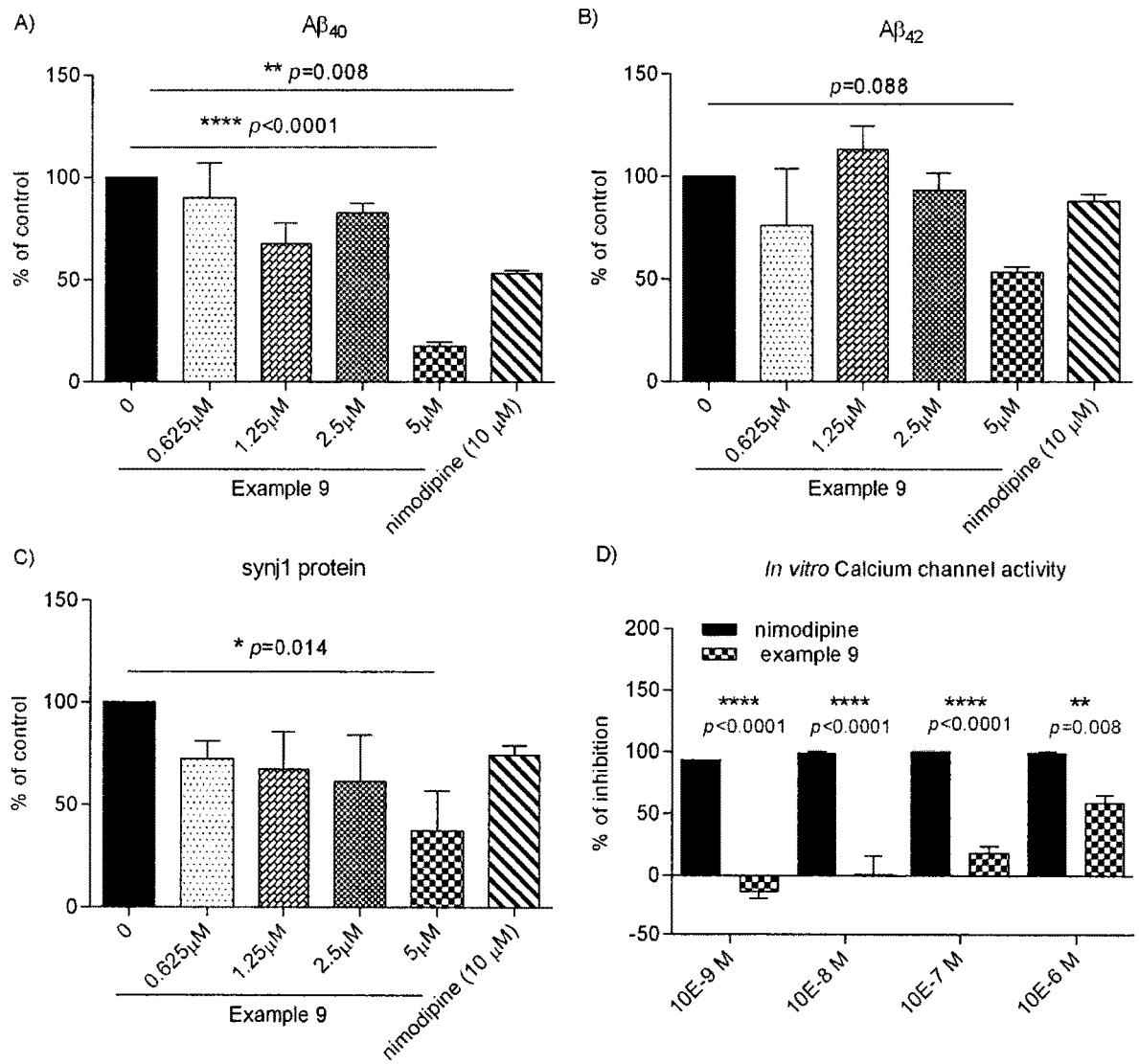
FIG. 3 compares the in vitro dose-dependent effects of a compound of the invention with nimodipine on lowering levels of A) $A\beta_{40}$, B) $A\beta_{42}$, and C) synj1 protein levels, and D) the inhibition of calcium channel activities, after incubation in wt cortical neuronal culture.

FIG. 3 Comparison of the AD- and synj1-lowering as well as CCB effects between Example 9 and nimodipine. Levels of A) Aβ$_{40}$, B) Aβ$_{42}$, and C) synj1 protein in drug-treated conditions (Example 9 dosage range 0.625-5 μM, nimodipine at 10 μM) for 72-96 hours. DMSO-treated conditions were used as controls and results were presented as percentage of the control (±SEM). In wt cortical neurons, nimodipine at 10 μM resulted in 47.0% reduction in Aβ$_{40}$ and 12.1% reduction in Aβ$_{42}$ with a concomitant reduction in synj1 levels (26.6%; FIGS. 3A, B and C). One structural derivative out of the 11 first-generation analogs synthesized exhibited more potent effects than nimodipine at reducing both Aβ$_{40}$ and Aβ$_{42}$ levels after 7-day treatment (Example 9; FIGS. 3A, B and C). At 5 μM of concentration, Example 9 exhibited 82.6% reduction in Aβ$_{40}$ and 46.6% reduction in Aβ$_{42}$ with 62.4% reduction in synj1 levels. D) In vitro calcium channel inhibition assays. Results were presented as percentage of inhibition (±SEM). Example 9 has attenuated calcium channel blockade effects (FIG. 3D) when compared to nimodipine. At 1 µM of Example 9, there was 41.3% reduction in its calcium channel blockade effects, and there was 81.3% reduction at 0.1 µM. One-way ANOVA was performed followed by post-hoc multiple comparison tests to determine the significance of differences between drug-treated vs DMSO control. *p<0.05, p<0.01, *p<0.001; N=3/condition except in A) nimodipine-treated conditions with N=20.

Figure 4:
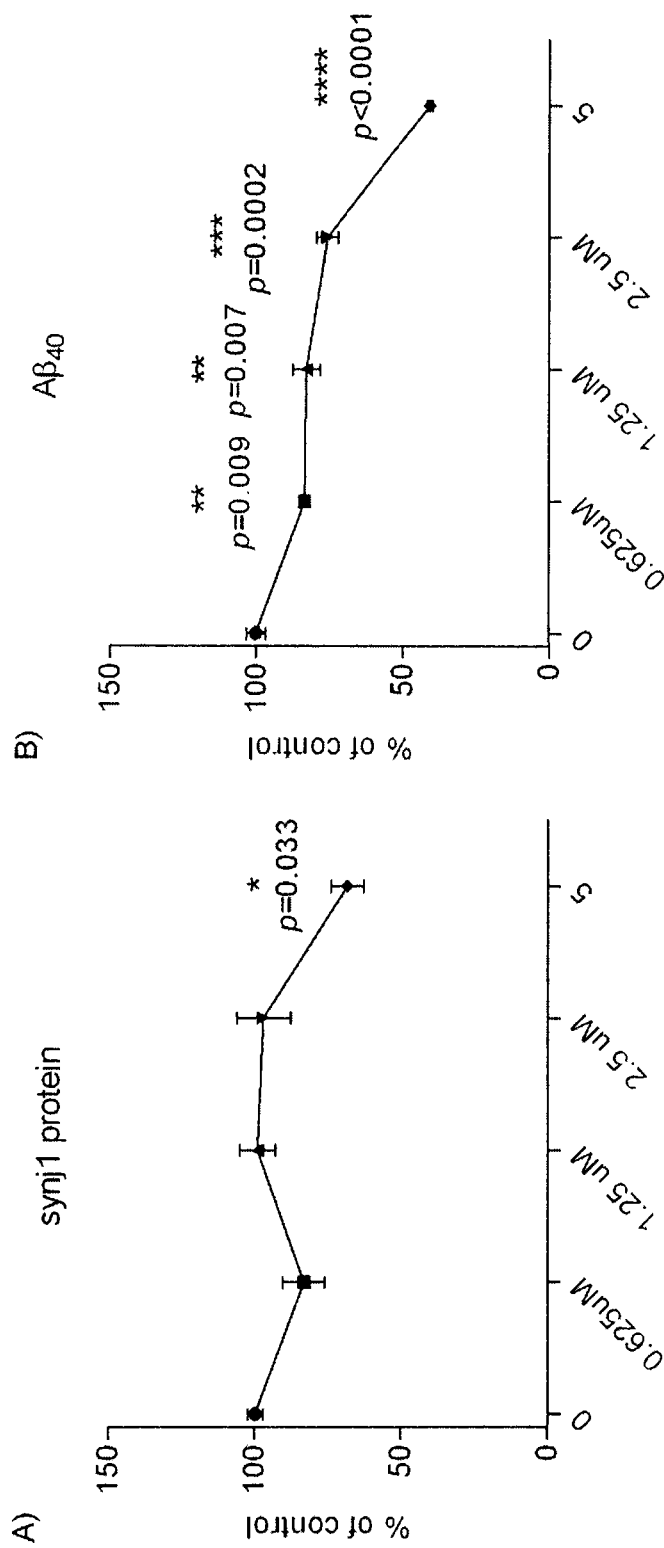
FIG. 4 shows the effect of a compound of the invention in ApeE4 neurons on A) synj1 and B) Aβ40 protein levels.

FIG. 4 Dose curve analysis of Aβ- and synj1-lowering effects of Example 9 in ApoE4 neurons. Embryonic day 17 old ApoE4 cortical neurons were incubated with Example 9 for 4-5 days before being subjected for Western blot analysis of synj1 protein levels as well as ELISA measurement of media $Aβ_{40}$ levels. Levels of A) synj1 protein and B) $Aβ_{40}$ in Example 9-treated conditions (dosage range 0.625-5 µM) for 72-96 hours in ApoE4 cortical neurons. DMSO-treated conditions were used as controls and results were presented as percentage of the control (±SEM). One-way ANOVA was performed followed by post-hoc multiple comparison tests to determine the significance of differences between drug-treated vs DMSO control. *p<0.05, p<0.01, *p<0.001, ****p<0.0001; N=6-15/condition.

Figure 5:
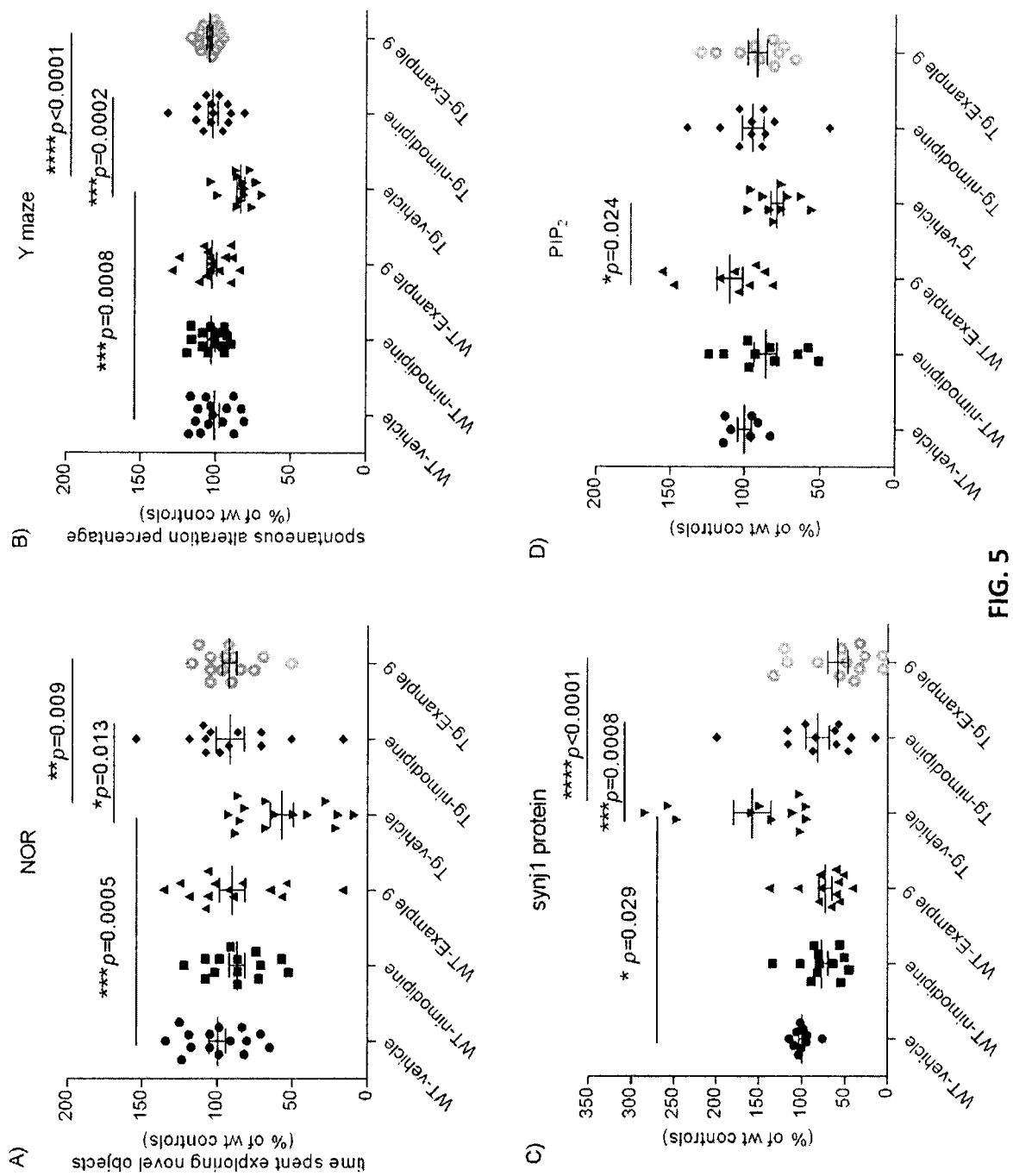
FIG. 5 shows the results of long-term in vivo treatment of daily IP injection of a compound of the invention in AD transgenic mice as compared with vehicle and nimodipine in A) Novel Object Recognition tests, B) Y maze, C) cortical brain synj1 levels, D) and cortical $PIP_2$ levels.

FIG. 5 Long-term in vivo treatment of nimodipine or Example 9 via daily IP injection at 2.5 mg/kg/day in AD transgenic mice. 2-3 months old AD transgenic mice were treated with vehicle, nimodipine or Example 9 at 2.5 mg/kg/day for 6 months via daily IP injection before subjected for behavior studies followed by biochemical analysis. A) NOR and B) Y maze tests show that, after nimodipine or Example 9 treatment for 6 months, there were cognitive improvements in AD transgenic mice (Tg Example 9) compared to vehicle (Tg DMSO) mice. Data is presented as % of wt control (vehicle-treated) time spent exploring novel objects. N=13-15/group. C) Cortical brain synj1 levels as well as D) $PIP_2$ levels in Tg mice (vehicle-, nimodipine- or Example 9-treated) were compared to vehicle-treated controls (as 100%) in wildtype (wt) mice. N=7-13/group. One-way ANOVA was performed followed by post-hoc multiple comparison tests to determine the significance of differences between pairs of means. *p<0.05, p<0.01, *p<0.001, ****p<0.0001.

Figure 6:
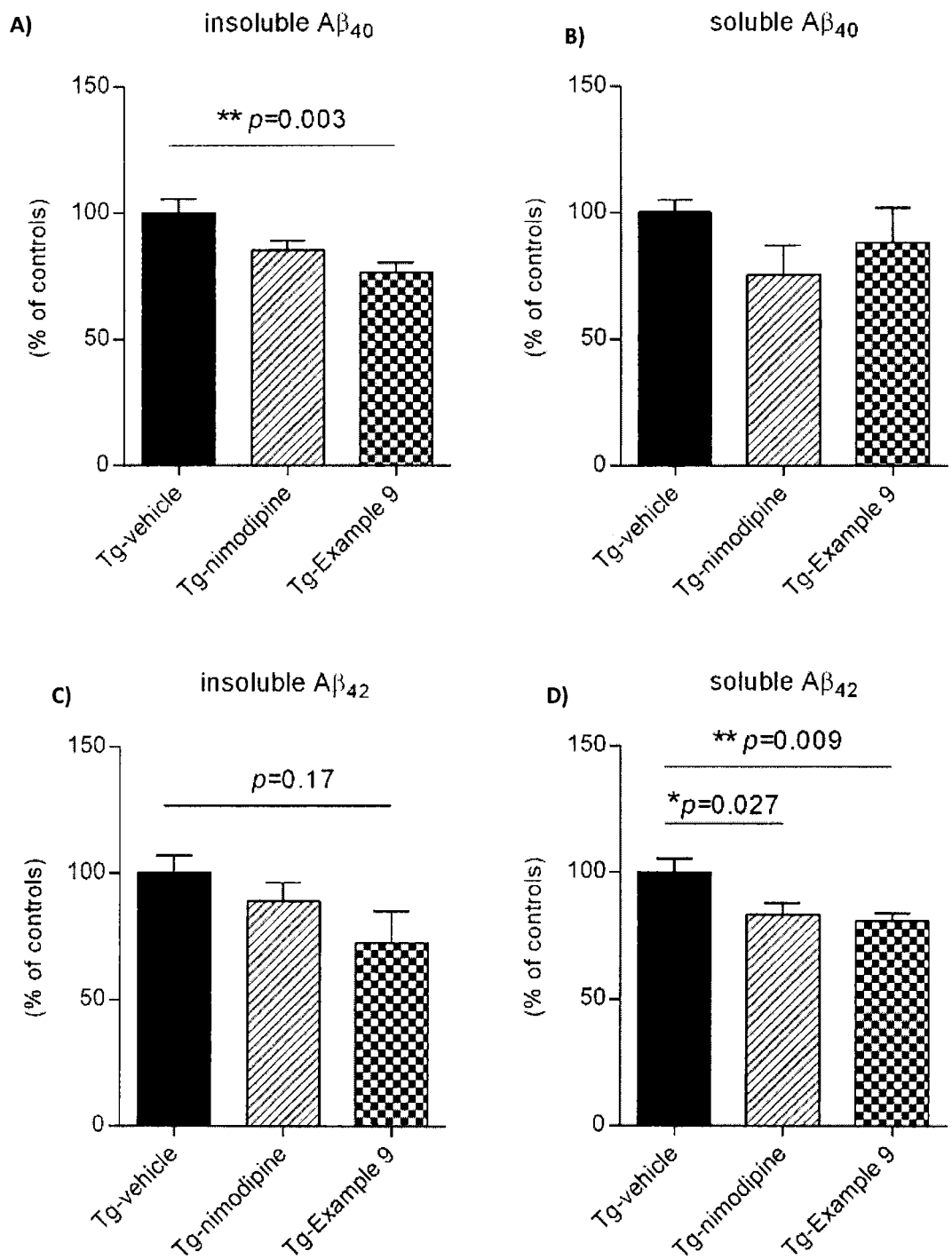
FIG. 6 shows levels of soluble and insoluble $A\beta_{42}$ and $A\beta_{40}$ with animal brains (cortical lysates) treated with a compound of the invention. A) Insoluble $A\beta_{40}$; B) Soluble $A\beta_{40}$; C) Insoluble $A\beta_{42}$; D) Soluble $A\beta_{42}$.

FIG. 6 Long-term in vivo treatment of nimodipine or Example 9 via daily IP injection at 2.5 mg/kg/day in AD transgenic mice. 2-3 months old AD transgenic mice were treated with vehicle, nimodipine or Example 9 at 2.5 mg/kg/day for 6 months via daily IP injection before subjected for behavior studies followed by biochemical analysis. Reduction in levels of insoluble Aβ340 and soluble $Aβ_{42}$ with Example 9 treated Tg animal brains. A trend of reduction in levels of insoluble $Aβ_{42}$ with Example 9 treatment was also seen. N=5-7/group. Vehicle-treated conditions were used as controls and results were presented as percentage of the control (±SEM). One-way ANOVA was performed followed by post-hoc multiple comparison tests to determine the significance of differences between drug-treated vs DMSO control. *p<0.05, **p<0.01.

Figure 7:
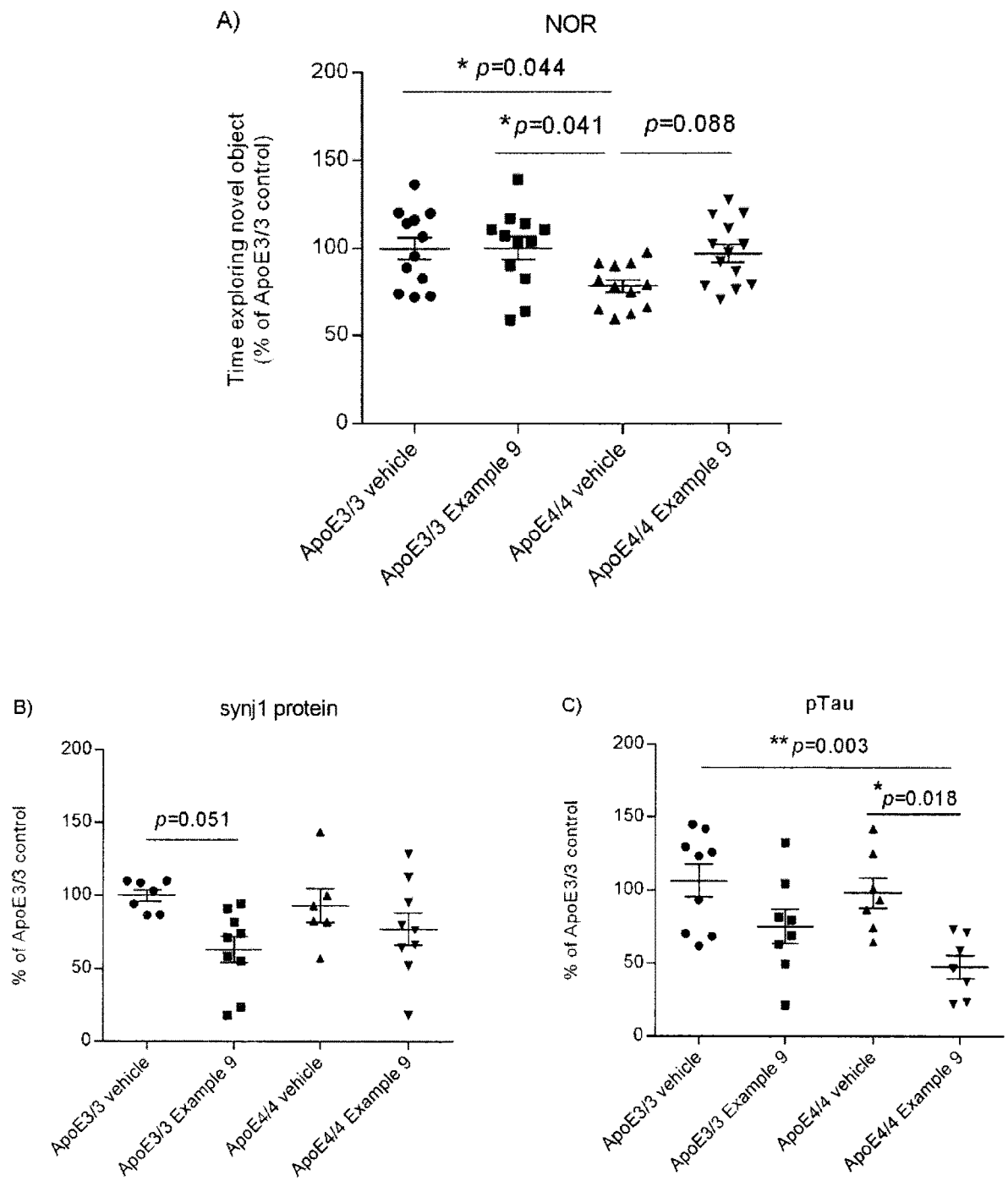
FIG. 7 shows the results of long-term in vivo treatment of daily oral administration of a compound of the invention in ApoE KI mice as compared with vehicle and nimodipine in A) Novel Object Recognition tests, B) cortical brain synj1 levels, and C) cortical brain pTau levels.

FIG. 7 Long-term in vivo treatment of Example 9 via daily oral administration at 3 mg/kg/day in ApoE KI mice. A) NOR tests show that after Example 9 treatment for 6-months, there were cognitive improvements in ApoE4 mice compared to vehicle-treated ApoE4 mice. Data is presented as a percentage of ApoE3 control (vehicle-treated) time spent exploring novel objects. N=12-13/group. Cortical brain B) synj1 levels as well as C) pTau levels in ApoE4 mice (vehicle- or Example 9-treated) were compared to vehicle-treated controls (as 100%) in ApoE3 mice. N=6-9/group. One-way ANOVA was performed followed by post-hoc multiple comparison tests to determine the significance of differences between pairs of means. *p<0.05, **p<0.01.

Figure 8:
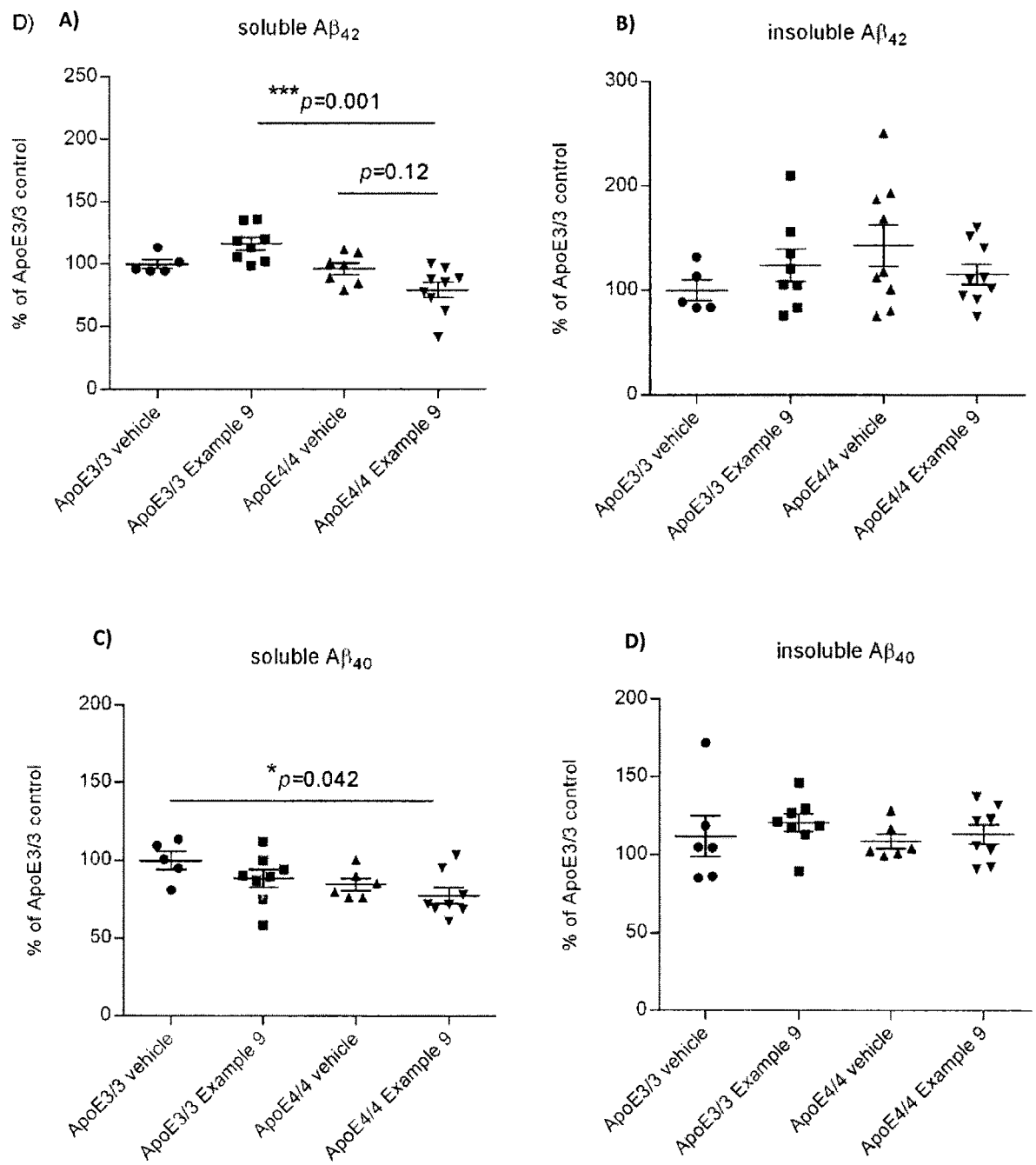
FIG. 8 illustrates the results of long-term in vivo treatment of daily oral administration of a compound of the invention in ApoE KI mice as compared with vehicle and nimodipine in soluble and insoluble $A\beta_{40}$ and $A\beta_{42}$ levels. A) Soluble $A\beta_{42}$; B) Insoluble $A\beta_{42}$; C) Soluble $A\beta_{40}$; D) Insoluble $A\beta_{40}$.

FIG. 8 Long-term in vivo treatment of Example 9 via daily oral administration at 3 mg/kg/day in ApoE KI mice. A reduction in levels of soluble $Aβ_{40}$ and $Aβ_{42}$ with Example 9-treated ApoE4 animal brains when compared to levels in vehicle-treated ApoE3 mouse brains was seen, and a trend of reduction in levels of insoluble $Aβ_{42}$ with Example 9 treatment was also seen. N=5-8/group. Vehicle-treated conditions were used as controls and results were presented as percentage of the control (±SEM). One-way ANOVA was performed followed by post-hoc multiple comparison tests to determine the significance of differences between drug-treated vs DMSO control. *p<0.05, ***p<0.001.

Figure 9:
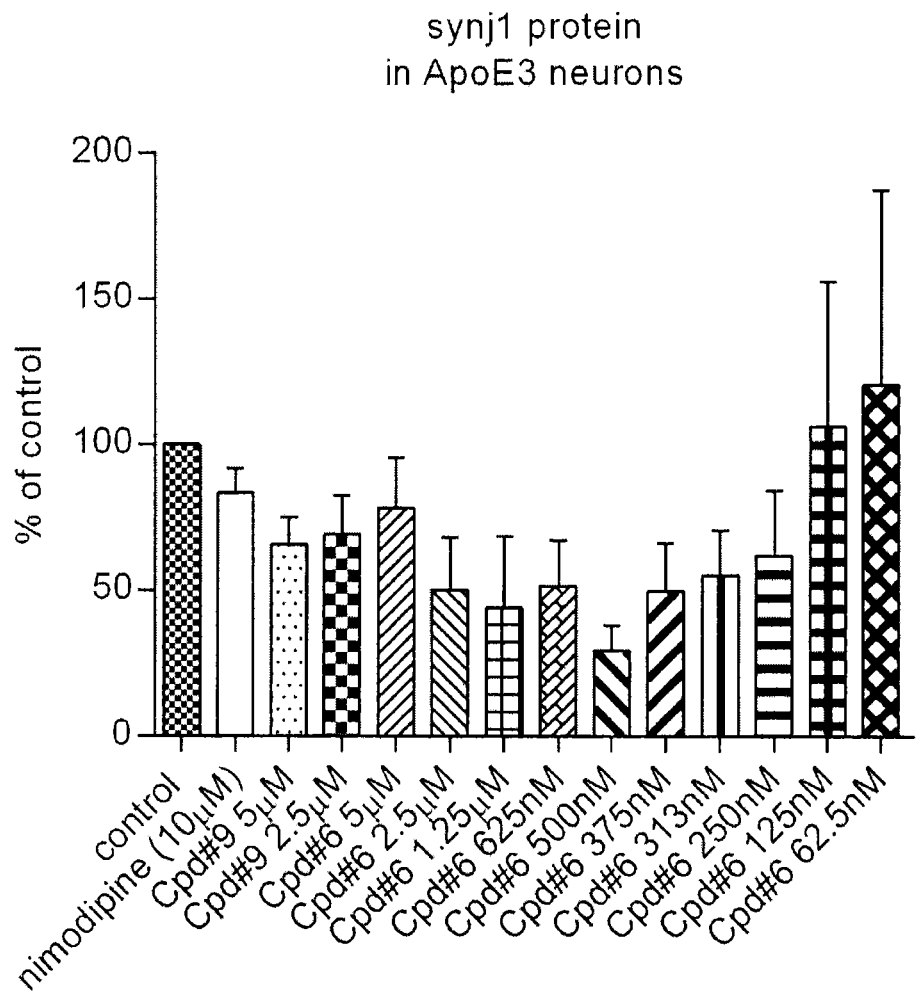
FIG. 9 shows the results of reduction of synj1 using compounds of the invention in comparison to vehicle and nimodipine in ApoE3 neurons.
Figure 10:
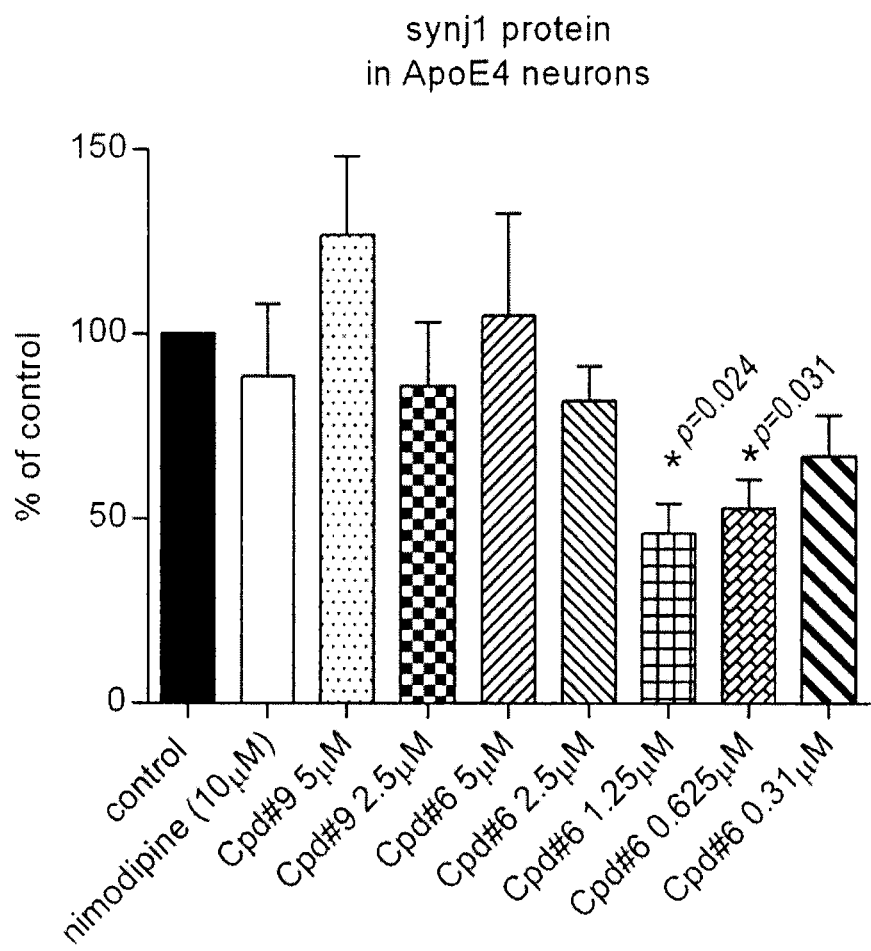
FIG. 10 shows the results of reduction of synj1 using compounds of the invention in comparison to vehicle and nimodipine in ApoE4 neurons.

FIG. 9 shows the results of reduction of synj1 using Example 6 and Example 9 in comparison to vehicle and nimodipine in ApoE3 neurons. Embryonic day 17 old ApoE3 cortical neurons were incubated with Example 6 and Example 9 for 7-9 days before being subjected for Western blot analysis of synj1 protein levels. DMSO-treated conditions were used as controls and results were presented as percentage of the control (±SEM). One-way ANOVA was performed followed by post-hoc multiple comparison tests to determine the significance of differences between drug-treated vs DMSO control. The effects of Cpd #6 at a dose range (62.5 nM-5 µM) were explored. A trend of reduction in synj1 levels is seen in ApoE3 neurons at 500 nM, but is not statistically significant at N=2. Example 6 at a lower dose range (62.5-625 nM) seems to reduce synj1 levels in ApoE3 neurons in a dose-dependent fashion. N=2-5/condition FIG. 10 shows the results of reduction of synj1 using Example 6 and Example 9 in comparison to vehicle and nimodipine in ApoE4 neurons. Embryonic day 17 old ApoE4 cortical neurons were incubated with Example 6 and Example 9 for 7-9 days before being subjected for Western blot analysis of synj1 protein levels. DMSO-treated conditions were used as controls and results were presented as percentage of the control (±SEM). One-way ANOVA was performed followed by post-hoc multiple comparison tests to determine the significance of differences between drug-treated vs DMSO control. Example 6 at 625 nM can reduce synj1 effectively in ApoE4 neurons (N=4). *p<0.05

Figure 11:
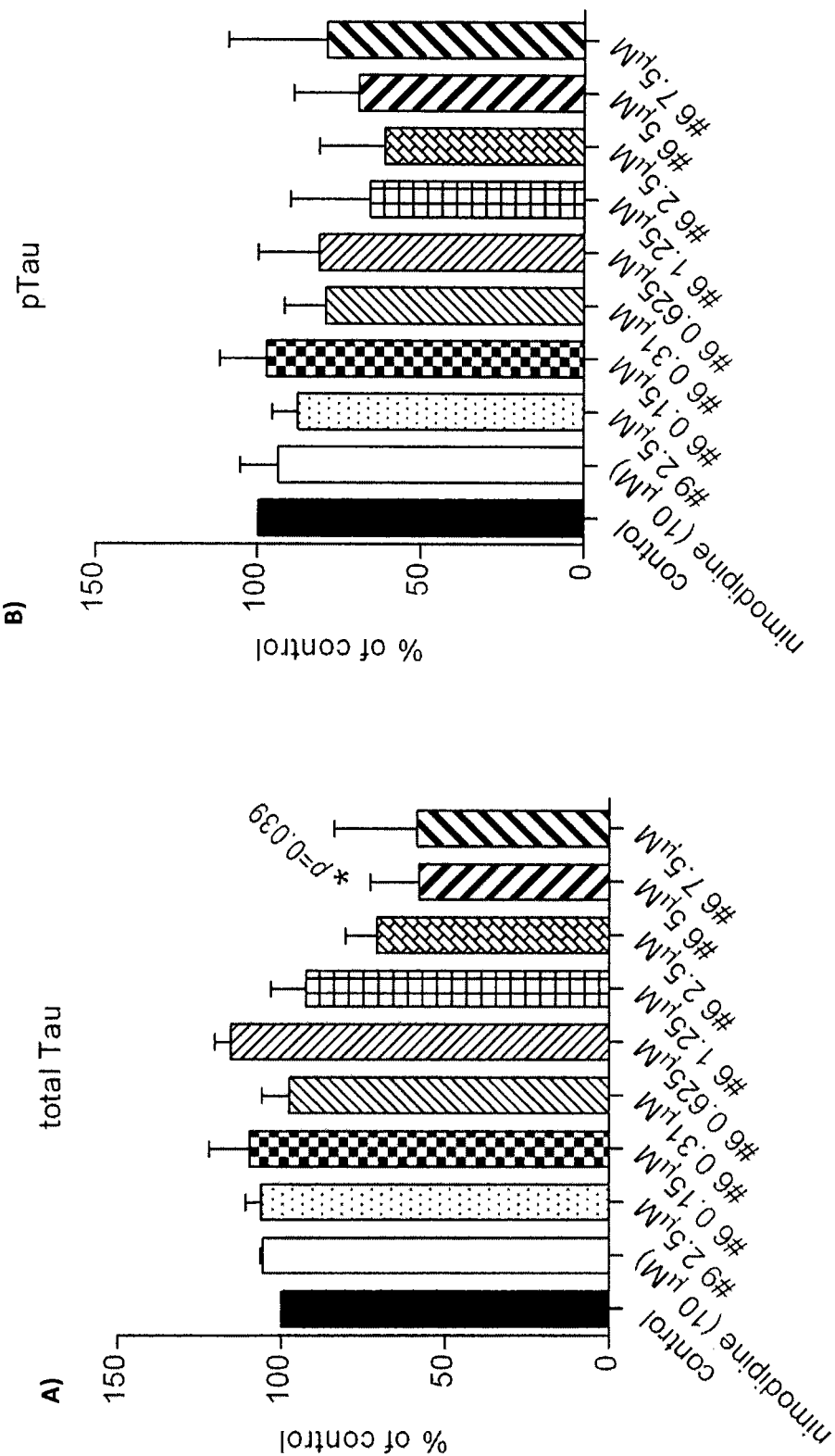
FIG. 11 shows the in vitro dose-dependent effects of a compound of the invention in comparison to vehicle on lowering levels of A) pTau and B) Tau in N2a cells expressing human wildtype Tau.

FIG. 11 shows the results of reduction of total Tau and pTau using Example 6 and Example 9 in comparison to vehicle and nimodipine in N2a cells expressing human Tau. N2a cells expressing human Tau were incubated with Example 6 and Example 9 for 7-9 days before being subjected for ELISA and Western blot analysis of Tau and pTau (Thr181) levels. DMSO-treated conditions were used as controls and results were presented as percentage of the control (±SEM). One-way ANOVA was performed followed by post-hoc multiple comparison tests to determine the significance of differences between drug-treated vs DMSO control. The effects of Example 6 were more potent than either Example 9 or nimodipine in lowering total Tau. A similar trend of increased potency with Example 6 was seen in lowering pTau levels when compared to Example 9 or nimodipine. *p<0.05, N=2-5/condition.

DMPK studies were performed with Example 9 in parallel with nimodipine. Both the CNS penetrability and the oral bioavailability of Example 9 were found to be better than nimodipine (TABLE III):

TABLE III: Compound profile and PK studies after oral delivery of 30 mg/kg in wt mice (Example 9 versus nimodipine).

TABLE IIIa

Blood pharmacokinetic parameters for #9 after IV(1 mg/kg) or PO(30 mg/kg) administration to Male CD-1 mice

| Dose Route | $T_{1/2}$ (h) | Cmax (ng/mL) | AUC (ng · h/mL) | Cl (L/h/kg) | Vss (L/kg) | % F |
|---|---|---|---|---|---|---|
| IV | 1.68 | 228 | 189 | 5.1 | 8.2 | — |
| PO | 0.84 | 1010 | 4115 | — | — | 73 |

TABLE IIIb

Brain and Blood Exposure of #9 after PO(30 mg/kg) administration to Male CD-1 mice

| Time (h) | Brain conc. (ng/mL) | Blood conc. (ng/mL) | Brain/Blood ratio |
|---|---|---|---|
| 1 | 604 | 518 | 1.2 |
| 3 | 421 | 607 | 0.7 |

TABLE IIIc

Blood pharmacokinetic parameters for #10 (rac. Nimodipine) after IV(1 mg/kg) or PO(30 mg/kg) administration to Male CD-1 mice

| Dose Route | $T_{1/2}$ (h) | Cmax (ng/mL) | AUC (ng · h/mL) | Cl (L/h/kg) | Vss (L/kg) | % F |
|---|---|---|---|---|---|---|
| IV | 0.58 | 341 | 187 | 5.33 | 3.29 | — |
| PO | 7.27 | 114 | 384 | — | — | 7 |

TABLE IIId

Brain and Blood Exposure of #10 (rac. Nimodipine) after PO(30 mg/kg) administration to Male CD-1 mice

| Time | Brain conc. (ng/mL) | Blood conc. (ng/mL) | Brain/Blood ratio |
|---|---|---|---|
| 1 | 136 | 70 | 1.9 |
| 3 | 62 | 62 | 1.0 |

The EFAD transgenic mouse model described in Tai et al. ("EFAD transgenic mice as a human APOE relevant preclinical model of Alzheimer's disease." J. Lipid Res. 2017. 58: 1733-1755) may also be used to test the efficacy of compounds of the invention. Many Alzheimer's disease symptoms and markers can be assessed using these transgenic mice, including (but not limited to) pTau, Aβ deposition, neuroinflammation, and behavioral deficits. Various experimental protocols for testing different parameters can be found in Tai et al. and its cited references.

Various embodiments of the invention can be described in the text below:

[1]. A compound of formula I, IA, or IB.

[2]. A compound according to [1] above, or according to other embodiments of the invention, wherein $R^1$ is hydrogen, $C_1$-$C_6$ alkyl, or $C_3$-$C_6$ cycloalkyl

[3]. A compound according to [1] or [2] above, or according to other embodiments of the invention, wherein $R^1$ is $C_1$-$C_6$ alkyl.

[4]. A compound according to [1], [2], or [3] above, or according to other embodiments of the invention, wherein $R^1$ is methyl, ethyl, n-propyl, or isopropyl.

[5]. A compound according to [1] or [2] above, or according to other embodiments of the invention, wherein $R^1$ is $C_3$-$C_6$ cycloalkyl.

[6]. A compound according to [1], [2], or [5] above, or according to other embodiments of the invention, wherein $R^1$ is cyclopropyl.

[7]. A compound according to any of [1] through [6] above, or according to other embodiments of the invention, wherein $R^2$ is hydrogen, halogen, $C_1$-$C_6$ alkyl, $C_3$-$C_6$ cycloalkyl, $C_1$-$C_6$ alkoxy, $C_1$-$C_6$ haloalkoxy, $C_1$-$C_6$ haloalkyl, nitro, cyano, $C_1$-$C_6$ alkylthio, and $C_1$-$C_6$ haloalkylthio.

[8]. A compound according to any of [1] through [7] above, or according to other embodiments of the invention, wherein $R^2$ is hydrogen, fluoro, chloro, methoxy, nitro, $C_1$-$C_3$ perfluoroalkyl, $C_1$-$C_3$ perfluoroalkoxy, t-butyl, n-propyl, isopropyl, ethyl, methyl, $C_1$-$C_6$ haloalkyl, or cyano.

[9]. A compound according to any of [1] through [8] above, or according to other embodiments of the invention, wherein $R^2$ is hydrogen, fluoro, chloro, methoxy, trifluoromethyl, trifluoromethoxy, or t-butyl.

[10]. A compound according to [9] above, or according to other embodiments of the invention, wherein $R^1$ is hydrogen or methyl; and $R^2$ is hydrogen, fluoro, chloro, methoxy, trifluoromethyl, trifluoromethoxy, or t-butyl.

[11]. A compound according to [10] above, or according to other embodiments of the invention, wherein $R^1$ is hydrogen; and $R^2$ is hydrogen, fluoro, chloro, methoxy, trifluoromethyl, trifluoromethoxy, or t-butyl.

[12]. A pharmaceutical composition comprising a pharmaceutically acceptable carrier and a compound of any one of [1] to [11] above, or according to other embodiments of the invention.

[13]. A method for treating a cognitive impairment or traumatic brain injury in a patient, comprising administering to the patient a therapeutically effective amount of a compound of any one of [1] to [11] above, or a pharmaceutical composition of [12] above, or according to other embodiments of the invention.

[14]. The method of [13] above, or according to other embodiments of the invention, wherein said cognitive impairment or traumatic brain injury is selected from Alzheimer's disease, mild cognitive impairment, Lewy body dementia (LBD), frontotemporal dementia (FTD), vascular dementia, mixed dementia, or Down Syndrome.

[15]. The method of [13] or [14] above, or according to other embodiments of the invention, wherein said cognitive impairment or traumatic brain injury is Alzheimer's disease.

[16]. The method of [13] above, or according to other embodiments of the invention, wherein said cognitive impairment or traumatic brain injury is traumatic brain injury.

[17]. A method of inhibiting synaptojanin 1 activity and/or expression, comprising administering to the patient a therapeutically effective amount of a compound of any one of [1] to [11] above, or a pharmaceutical composition of [12] above, or according to other embodiments of the invention.

[18]. A method of selectively inhibiting synaptojanin 1, comprising contacting the synaptojanin 1 with an amount of a compound of any one of [1] to [11] above, or a pharmaceutical composition of [12] above, or according to other embodiments of the invention, less than the amount required to inhibit calcium channels.

[19]. A method for treating a disease or disorder in a patient comprising down-regulating synaptojanin 1, comprising administering to the patient a therapeutically effective amount of a compound of any one of [1] to [11] above, or a pharmaceutical composition of [12] above, or according to other embodiments of the invention.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. A compound having a structure represented by a formula:

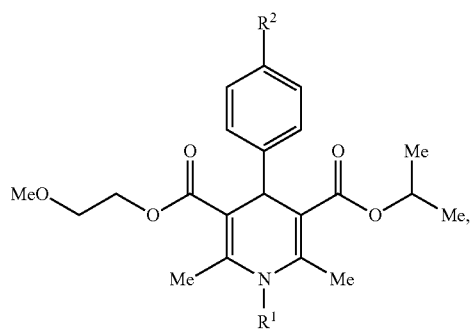

wherein
  $R^1$ is selected from hydrogen, $C_1$-$C_6$ alkyl, and $C_3$-$C_6$ cycloalkyl; and
  $R^2$ is selected from hydrogen, halogen, $C_1$-$C_6$ alkyl, $C_3$-$C_6$ cycloalkyl, $C_1$-$C_6$ alkoxy, $C_1$-$C_6$ haloalkoxy, $C_1$-$C_6$ haloalkyl, nitro, cyano, $C_1$-$C_6$ alkylthio, and $C_1$-$C_6$ haloalkylthio;
with the provisos that:
  when $R^1$ is hydrogen, $R^2$ is not chloro;
  when $R^1$ is methyl, $R^2$ is not trifluoromethyl, trifluoromethoxy, cyano, chloro, or fluoro;
  when $R^1$ is cyclopropyl, $R^2$ is not trifluoromethyl or trifluoromethoxy; and
  when $R^1$ is ethyl, $R^2$ is not trifluoromethyl or trifluoromethoxy,
or a pharmaceutically acceptable salt thereof.

2. The compound of claim 1, wherein $R^1$ is isopropyl.

3. The compound of claim 1, wherein $R^1$ is hydrogen.

4. The compound of claim 1, wherein $R^2$ is selected from $C_1$-$C_6$ alkyl, $C_3$-$C_6$ cycloalkyl, $C_1$-$C_6$ alkoxy, and nitro.

5. The compound of claim 4, wherein $R^2$ is selected from methyl, methoxy, t-butyl, and nitro.

6. The compound of claim 1, wherein $R^1$ is selected from hydrogen and isopropyl; and $R^2$ is selected from methyl, methoxy, t-butyl, and nitro.

7. The compound of claim 6, wherein $R^1$ is hydrogen.

8. The compound of claim 1, wherein the compound is selected from:

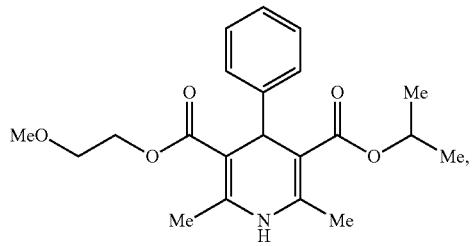

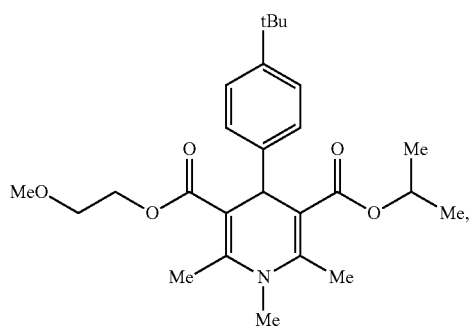

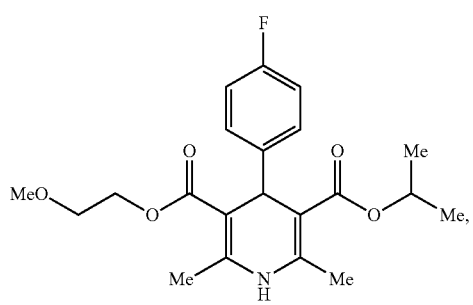

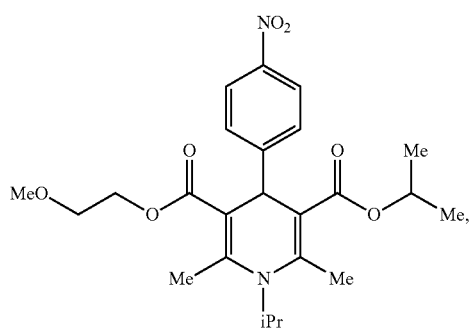

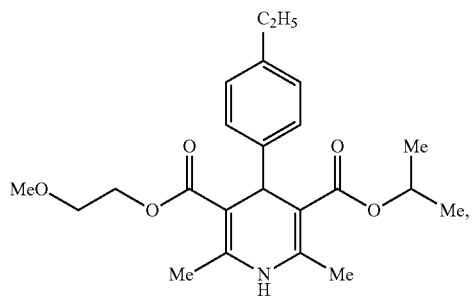

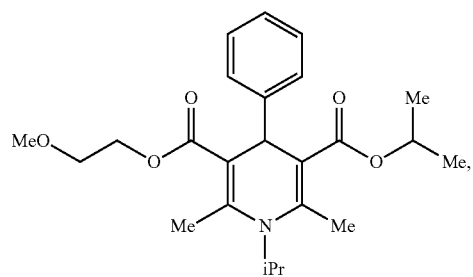
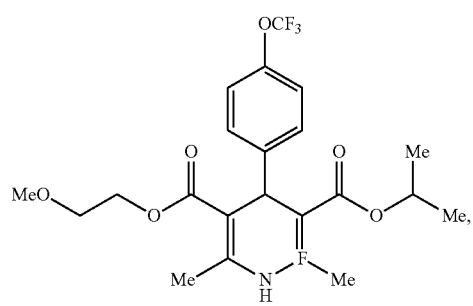
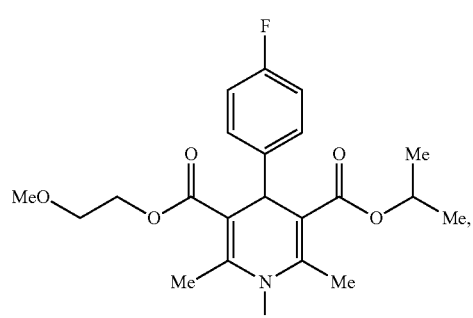
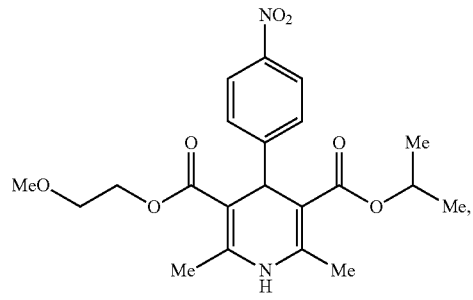
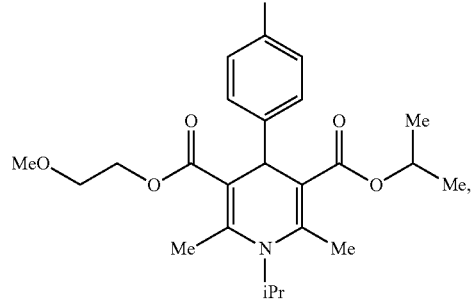
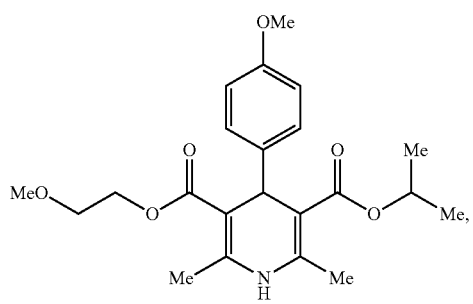
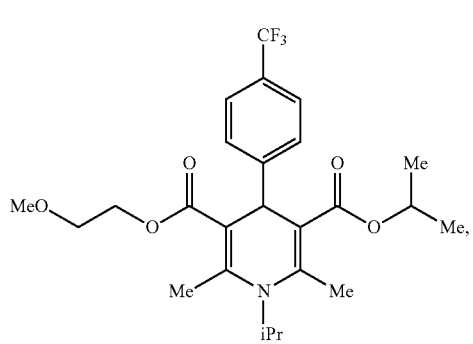
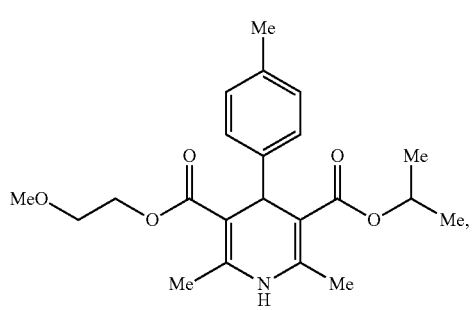
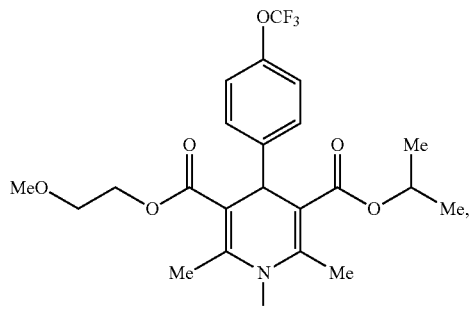
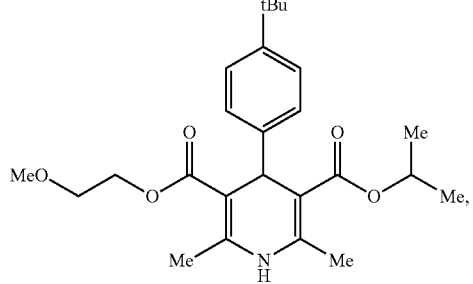

-continued
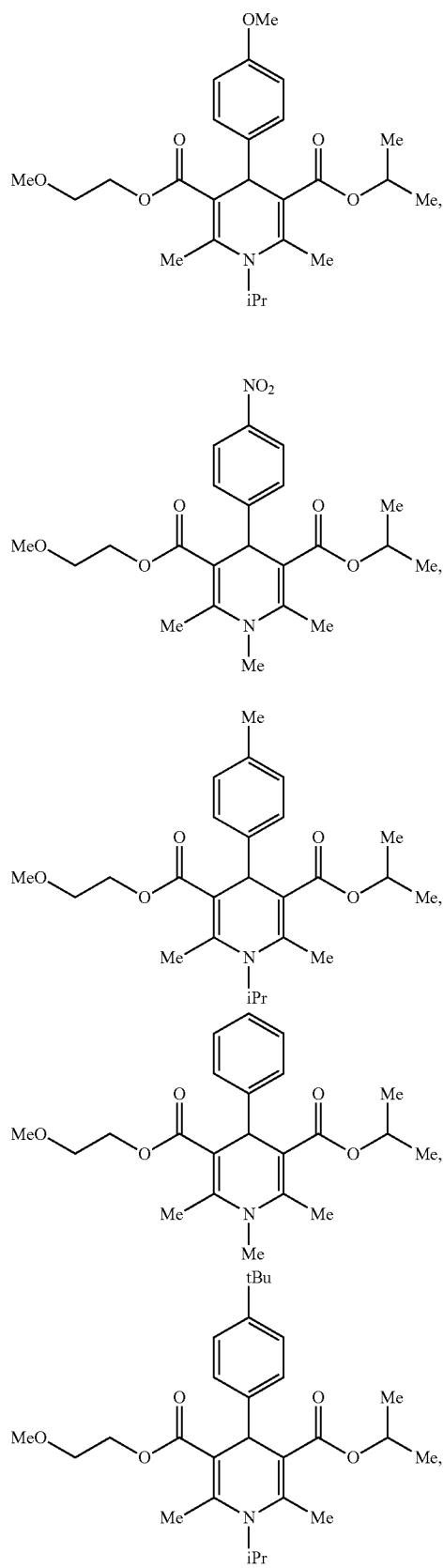
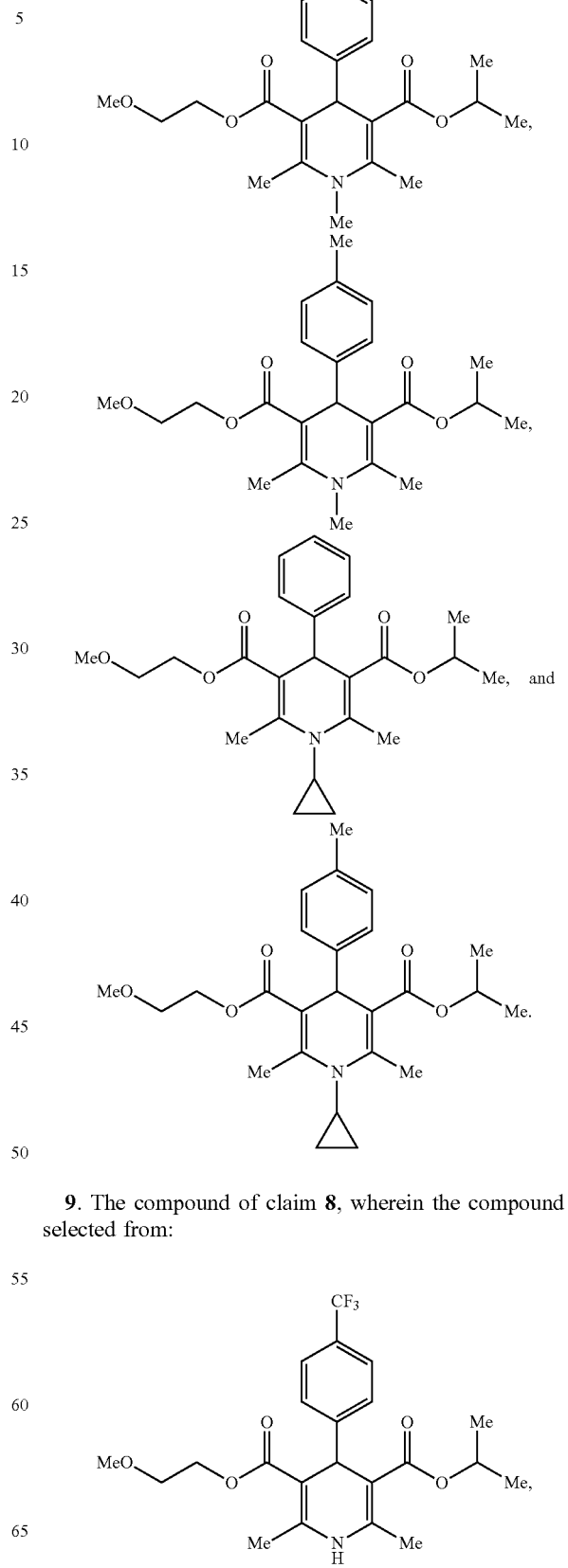
9. The compound of claim 8, wherein the compound is selected from:
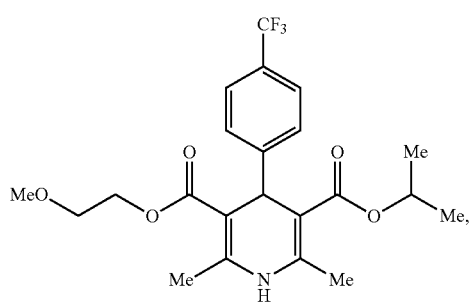

-continued
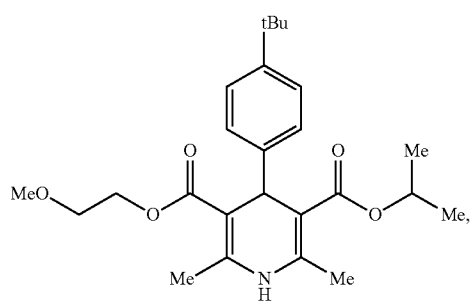 [SMILES: COCCOC(=O)C1=C(C)NC(C)=C(C(=O)OC(C)C)C1c1ccc(C(F)(F)F)cc1]
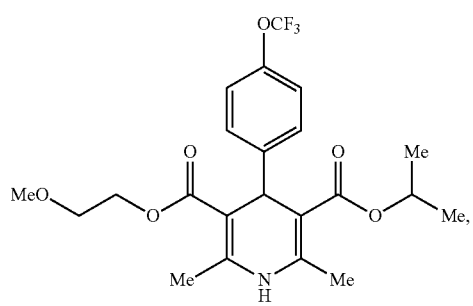
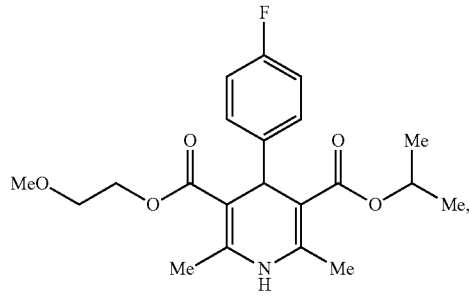
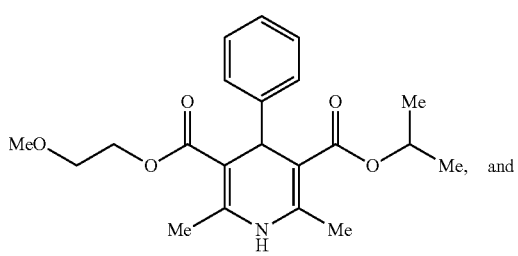 and
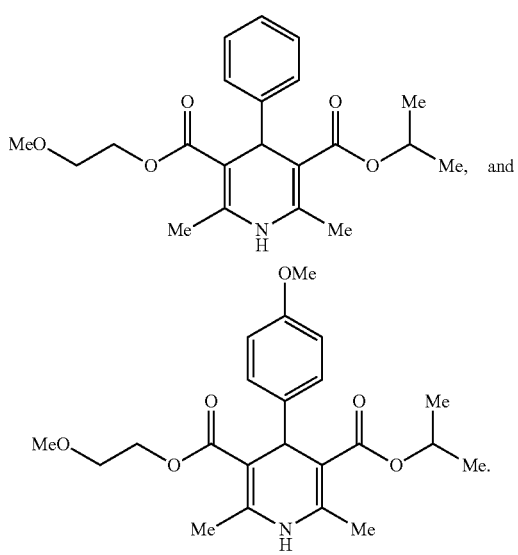
10. The compound of claim 9, wherein the compound is:
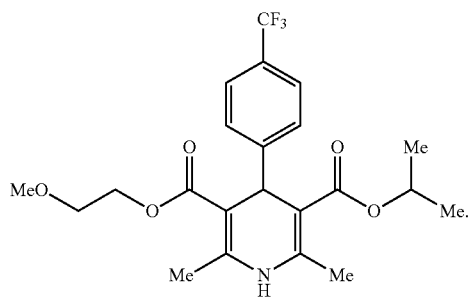
11. The compound of claim 9, wherein the compound is:
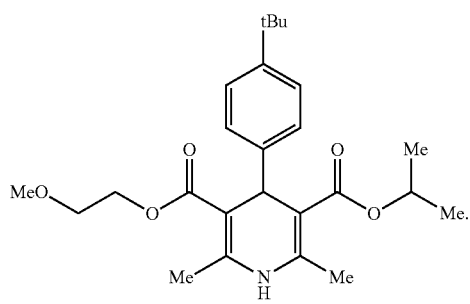 [SMILES: COCCOC(=O)C1=C(C)NC(C)=C(C(=O)OC(C)C)C1c1ccc(C(C)(C)C)cc1]
12. The compound of claim 1, wherein the compound has a structure represented by a formula:
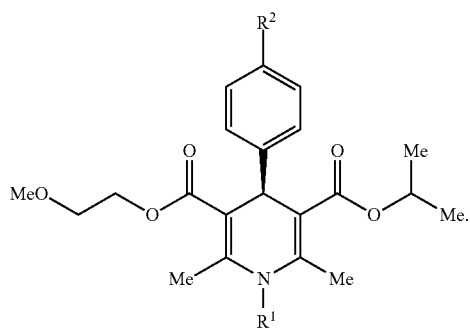
13. The compound of claim 1, wherein the compound has a structure represented by a formula:
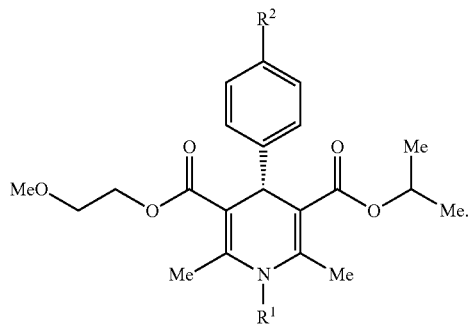

14. A pharmaceutical composition comprising a pharmaceutically acceptable carrier and an effective amount of the compound of claim 1.

15. A method for treating cognitive impairment or traumatic brain injury in a patient, comprising administering to the patient a therapeutically effective amount of the compound of claim 1.

16. The method of claim 15, wherein said cognitive impairment or traumatic brain injury is selected from Alzheimer's disease, mild cognitive impairment, Lewy body dementia (LBD), frontotemporal dementia (FTD), vascular dementia, mixed dementia, or Down Syndrome.

17. The method of claim 16, wherein said cognitive impairment or traumatic brain injury is Alzheimer's disease.

18. The method of claim 15, wherein said cognitive impairment or traumatic brain injury is traumatic brain injury.

19. The method of claim 15, wherein $R^1$ is selected from hydrogen and isopropyl; and $R^2$ is selected from methyl, methoxy, t-butyl, and nitro.

20. The method of claim 15, wherein the compound is selected from:

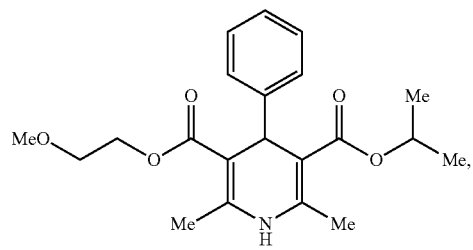

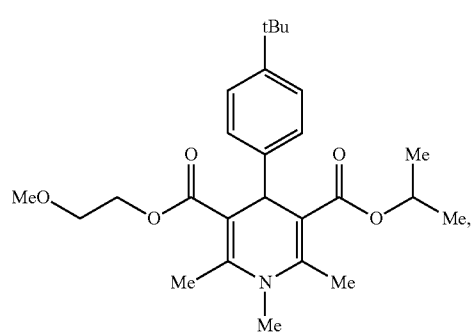

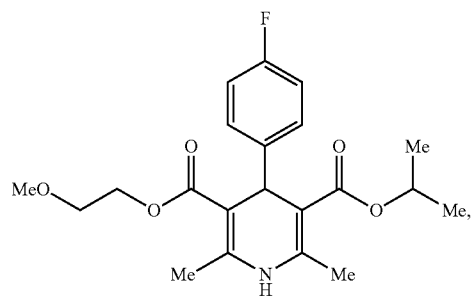

-continued

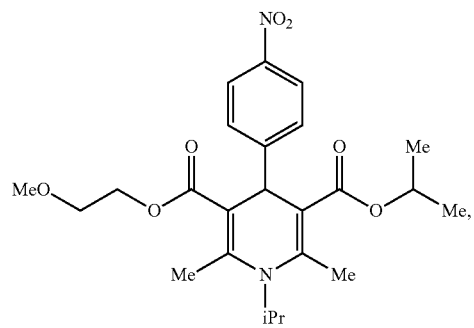

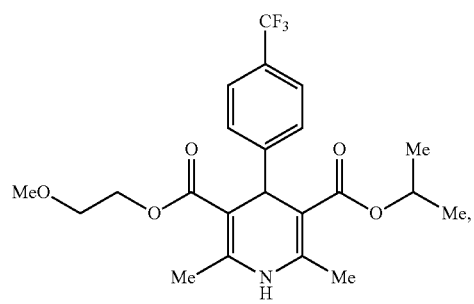

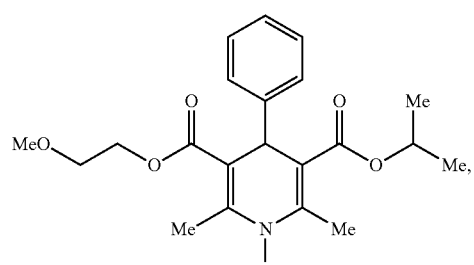

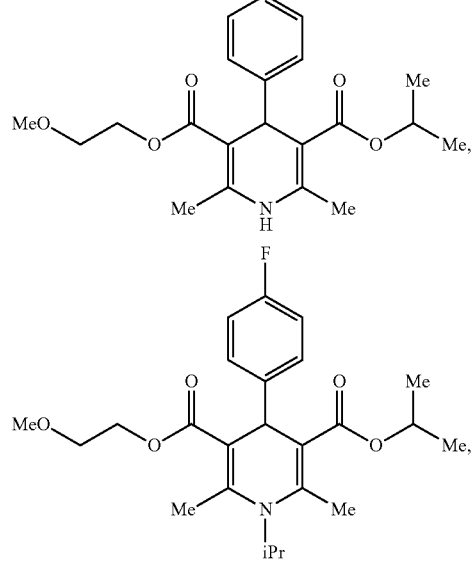

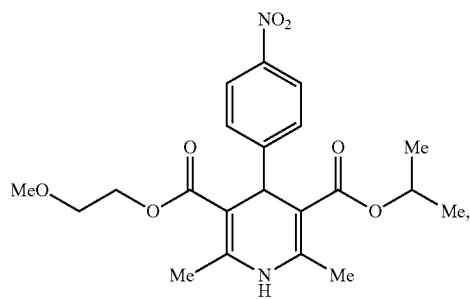
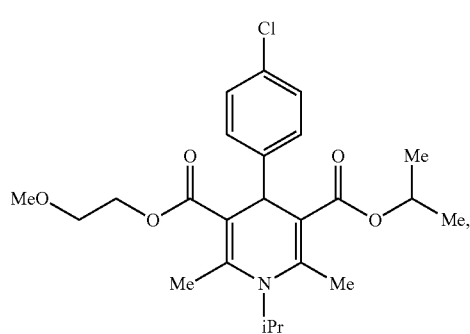
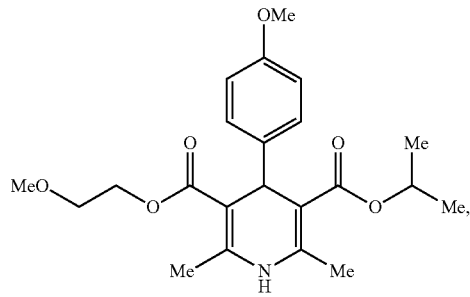
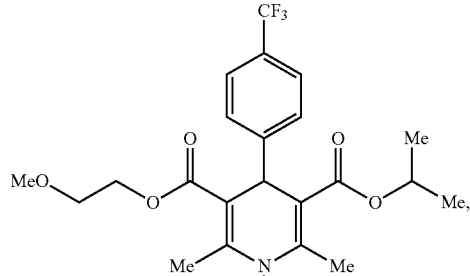
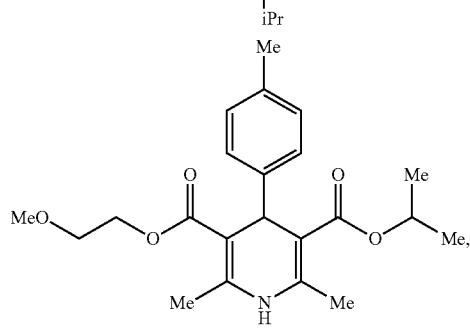
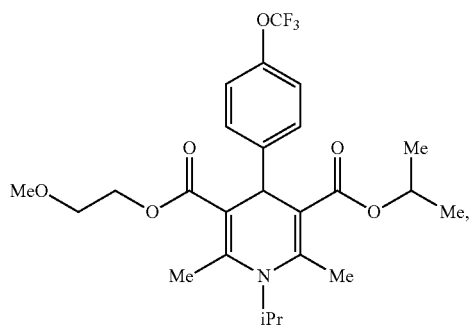
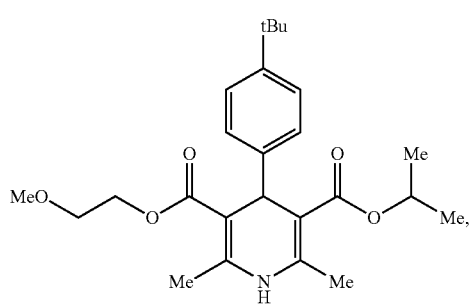
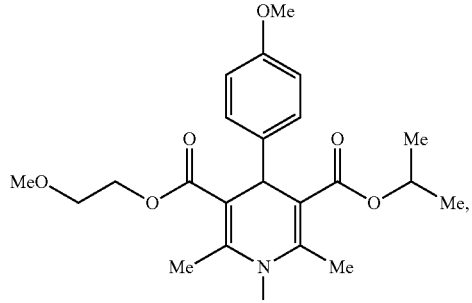
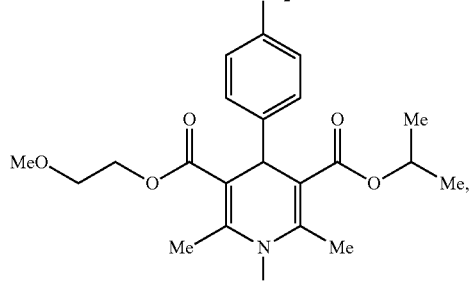
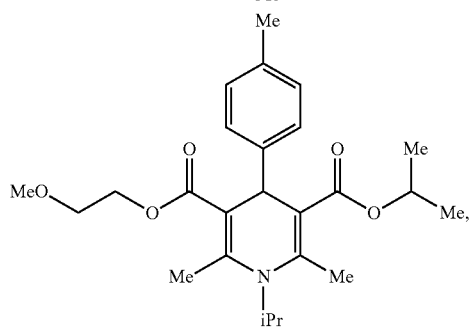

-continued
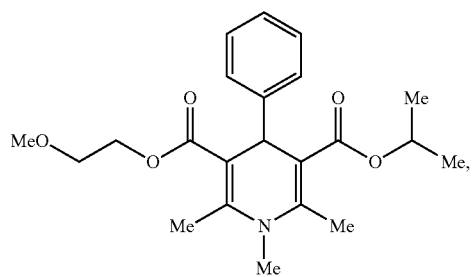
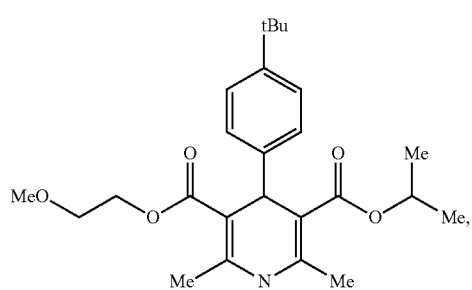
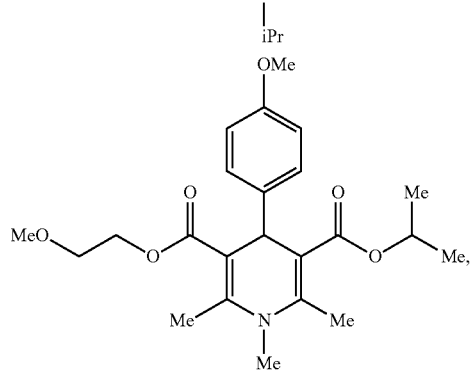
-continued
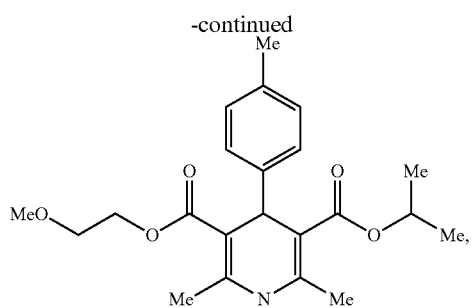
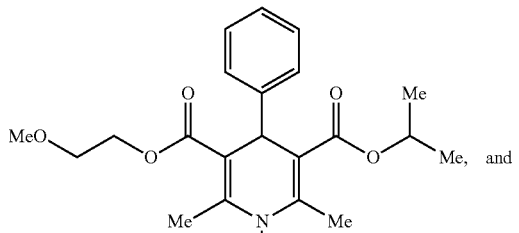
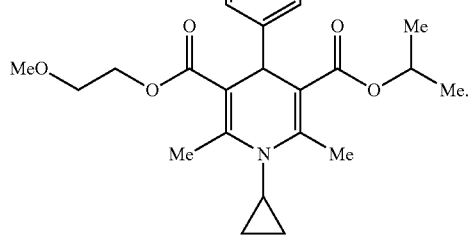
* * * * *